United States Patent [19]

Masuda et al.

[11] Patent Number: 6,090,815

[45] Date of Patent: Jul. 18, 2000

[54] PYRIMIDINYLOXYALKANOIC AMIDE DERIVATIVES AND FUNGICIDES FOR AGRICULTURAL AND HORTICULTURAL USE

[75] Inventors: Katsumi Masuda; Ikumi Urushibata; Tsuyoshi Asahara, all of Iwata-gun; Katsumi Furuse, Ogasa-gun; Yoshiyuki Kojima; Norimichi Muramatsu, both of Kakegawa, all of Japan

[73] Assignees: Kumiai Chemical Industry Co., Ltd.; Ihara Chemical Industry Co., Ltd., both of Tokyo, Japan

[21] Appl. No.: 09/297,066

[22] PCT Filed: Oct. 30, 1997

[86] PCT No.: PCT/JP97/03945

§ 371 Date: Apr. 30, 1999

§ 102(e) Date: Apr. 30, 1999

[87] PCT Pub. No.: WO98/18766

PCT Pub. Date: May 7, 1998

[30] Foreign Application Priority Data

Oct. 31, 1996 [JP] Japan ................................. 8-305693

[51] Int. Cl.[7] .................... A01N 43/59; C07D 239/30; C07D 239/34; C07D 239/38; C07D 239/88

[52] U.S. Cl. ...................... 514/259; 514/269; 544/287; 544/319; 544/320

[58] Field of Search ..................... 544/319, 320, 544/287; 514/259, 269

[56] References Cited

FOREIGN PATENT DOCUMENTS 62-42974  2/1987  Japan .

*Primary Examiner*—Mukund J. Shah
*Assistant Examiner*—Venkataraman Balasubramanian
*Attorney, Agent, or Firm*—Oblon, Spivak, McClelland, Maier & Neustadt, P.C.

[57] ABSTRACT

The present invention provides a pyrimidinyloxyalkanamide derivative represented by Formula (I):

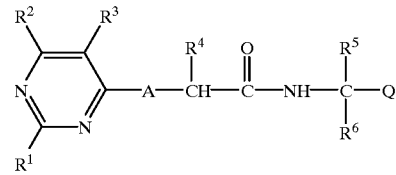

(I)

(wherein $R^1$ represents a hydrogen atom, a $C_1$–$C_6$ alkyl group, a $C_3$–$C_6$ cycloalkyl group, or the like, $R^2$ represents a $C_1$–$C_6$ alkyl group, a $C_1$–$C_4$ haloalkyl group, or the like, $R^3$ represents a hydrogen atom, a $C_1$–$C_6$ alkyl group, a halogen atom, or the like, $R^4$ represents a hydrogen atom, a $C_1$–$C_6$ alkyl group, or the like, Q represents a cyano group, a $C_1$–$C_6$ alkoxycarbonyl group, or the like, and A represents an oxygen atom or a sulfur atom) and a novel agricultural or horticultural fungicide including the same as an active ingredient.

The agricultural or horticultural fungicides according to the present invention have excellent controlling effects with regard to rice blast, which are apparently excellent controlling effects as compared with the known compounds. In addition, the agricultural or horticultural fungicides of the present invention also exhibit excellent residual activity, as well as persistence after rain without any negative effects on the subject plants.

22 Claims, No Drawings

PYRIMIDINYLOXYALKANOIC AMIDE DERIVATIVES AND FUNGICIDES FOR AGRICULTURAL AND HORTICULTURAL USE

TECHNICAL FIELD

The present invention relates to novel pyrimidinyloxyalkanamide derivatives and agricultural or horticultural fungicides containing the same as active ingredients.

BACKGROUND ART

Japanese Patent Application, First Publication, No. Sho 63-132867 discloses that aryloxycarboxylic acid derivatives have fungicidal activities. In the previous application, compounds having 2-pyrimidinyl group without any substituents in the aryl group are disclosed; however, they do not exhibit adequate fungicidal activities. In addition, there is no disclosure of compounds having 4-pyrimidinyl group with substituents.

Recently, conventional fungicides may not exhibit adequate fungicidal activities because of the emergence of resistant fungi after repeated use of the fungicides. In addition, as well as because of environmental problems, it is desired to provide novel fungicides which can efficiently control harmful fungi even at low concentrations. The present invention provides novel pyrimidinyloxyalkanamide derivatives exhibiting superior fungicidal activities.

Therefore, the present inventors have synthesized various novel pyrimidinyloxyalkanamide derivatives and have carried out extensive research in connection with their effects on the biological activities of fungi. As a result, the present inventors have found that the novel compounds according to the present invention have wide spectrum of fungicidal activity, and exhibit excellent fungicidal activities with regard to rice blast and the like, while at the same time do not hinder desirable plant growth.

DISCLOSURE OF THE INVENTION

The present invention provides pyrimidinyloxyalkanamide derivatives represented by Formula (I):

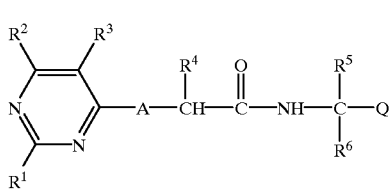

{wherein $R^1$ represents a hydrogen atom, a $C_1$–$C_6$ alkyl group, a $C_3$–$C_6$ cycloalkyl group, a C–$C_4$ haloalkyl group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a $C_1$–$C_6$ alkylthio group, a $C_1$–$C_6$ alkylsulfinyl group, a $C_1$–$C_6$ alkylsulfonyl group, a $C_2$–$C_6$ alkenylthio group, a $C_2$–$C_6$ alkynylthio group, a $C_3$–$C_6$ cycloalkylthio group, a $C_1$–$C_6$ alkylamino group, a di($C_1$–$C_6$ alkyl)amino group, a halogen atom, a phenyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), or a phenoxy group (which may be substituted by a $C_1$–$C_6$ alkyl group, a $C_1$–$C_4$ haloalkyl group, a $C_1$–$C_6$ alkoxy group, a cyano group, a nitro group, or a halogen atom), $R^2$ represents a hydrogen atom, a $C_1$–$C_6$ alkyl group, a $C_2$–$C_6$ alkenyl group, a $C_2$–$C_6$ alkynyl group, a $C_3$–$C_6$ cycloalkyl group, a $C_1$–$C_4$ haloalkyl group, a $C_2$–$C_6$ haloalkenyl group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a $C_1$–$C_4$ haloalkoxy group, a $C_1$–$C_6$ alkylthio group, a $C_2$–$C_6$ alkenylthio group, a $C_2$–$C_6$ alkynylthio group, a $C_1$–$C_6$ alkylamino group, a di($C_1$–$C_6$ alkyl)amino group, a halogen atom, or a phenyl group (which may be substituted by a $C_1$–$C_6$ alkyl group, a $C_1$–$C_4$ haloalkyl group, a $C_1$–$C_6$ alkoxy group, a cyano group, a nitro group, or a halogen atom), $R^3$ represents a hydrogen atom, a $C_1$–$C_6$ alkyl group, a $C_3$–$C_6$ cycloalkyl group, a $C_1$–$C_4$ haloalkyl group, a $C_1$–$C_6$ alkoxy group, a ($C_1$–$C_6$ alkyl)carbonyl group, a ($C_1$–$C_6$ alkoxy)carbonyl group, a halogen atom, a nitro group, or a cyano group, or $R^2$ and $R^3$, together with the carbon atom to which they are bonded, form a saturated 6-membered ring or an unsaturated 5-membered or 6-membered ring, $R^4$ represents a hydrogen atom, a $C_1$–$C_6$ alkyl group, a $C_3$–$C_6$ cycloalkyl group, or a $C_1$–$C_4$ haloalkyl group, $R^5$ and $R^6$ represents independently a hydrogen atom, a $C_1$–$C_6$ alkyl group, a $C_2$–$C_6$ alkenyl group, a $C_3$–$C_6$ cycloalkyl group (which may be substituted by a halogen atom or a $C_1$–$C_6$ alkyl group), a $C_3$–$C_6$ cycloalkyl $C_1$–$C_6$ alkyl group, a Ci –$C_6$ alkoxy $C_1$–$C_6$ alkyl group, or a $C_1$–$C_4$ haloalkyl group, $R^5$ and $R^6$, together with the carbon atom to which they are bonded, form a 5-membered~7-membered cycloalkyl group (which may be substituted by a $C_1$–$C_6$ alkyl group), or a hetrocyclyl group (which may be substituted by a $C_1$–$C_6$ alkyl group), Q represents a cyano group or a group of a formula: —$COR^7$ [wherein $R^7$ represents a $C_1$–$C_6$ alkyl group, a $C_3$–$C_6$ cycloalkyl group (which may be substituted by a halogen atom or a $C_1$–$C_6$ alkyl group), a $C_1$–$C_4$ haloalkyl group, a $C_1$–$C_6$ alkoxy group, a $C_2$–$C_6$ alkenyloxy group, a $C_2$–$C_6$ alkynyloxy group, or a $C_3$–$C_6$ cycloalkyloxy group], and A represents an oxygen atom or a sulfur atom}, as well as an agricultural or horticultural fungicide including the pyrimidinyloxyalkanamide derivative as an active ingredient.

The terms employed in the present invention are defined in the following. In the present invention, for example, in the case of the expression "$C_1$–$C_6$", the group shown after "$C_1$–$C_6$" has 1 to 6 carbon atoms.

The term "$C_1$–$C_6$ alkyl group" is used herein to mean a straight-chain or branched alkyl group including, for example, a methyl group, ethyl group, n-propyl group, isopropyl group, in-butyl group, isobutyl group, sec-butyl group, tert-butyl group, n-pentyl group, isopentyl group, neopentyl group, n-hexyl group, isohexyl group, 3,3-dimethylbutyl group, or the like.

As the term "$C_3$–$C_6$ cycloalkyl group", there can be mentioned, for example, a cyclopropyl group, cyclopentyl group, cyclohexyl group, or the like.

As the term "$C_3$–$C_6$ cycloalkyl $C_1$–$C_6$ alkyl group", there can be mentioned, for example, a cyclopropylmethyl group, cyclopentylmethyl group, cyclohexylmethyl group, or the like.

The term "$C_1$–$C_4$ haloalkyl group" is used herein to mean a halogen-substituted straight-chain or branched alkyl group including, for example, a fluoromethyl group, chloromethyl group, bromomethyl group, difluoromethyl group, dichloromethyl group, dibromomethyl group, trifluoromethyl group, chlorodifluoromethyl group, pentafluoroethyl group, or the like.

The term "$C_2$–$C_6$ alkenyl group" is used herein to mean a straight-chain or branched alkenyl group including, for example, a vinyl group, 1-propenyl group, allyl group, isopropenyl group, 1-butenyl group, 2-butenyl group, or the like.

The term "$C_2$–$C_6$ alkynyl group" is used herein to mean a straight-chain or branched alkynyl group including, for example, an ethynyl group, 1-propynyl group, 2-propynyl group, 1-butynyl group, 2-butynyl group, 3-butynyl group, 4-methyl-1-pentynyl group, 3-methyl-1-pentynyl group, or the like.

The term "halogen atom" is used herein to mean a fluorine atom, chlorine atom, bromine atom, or iodine atom.

The term "$C_1$–$C_6$ alkoxy group" is used herein to mean a straight-chain or branched alkoxy group including, for example, a methoxy group, ethoxy group, n-propoxy group, isopropoxy group, n-butoxy group, isobutoxy group, sec-butoxy group, tert-butoxy group, n-pentyloxy group, isopentyloxy group, n-hexyloxy group, or the like.

The term "$C_2$–$C_6$ alkenyloxy group" is used herein to mean a straight-chain or branched alkenyloxy group including, for example, an allyloxy group, isopropenyloxy group, 2-butenyloxy group, or the like.

The term "$C_2$–$C_6$ alkynyloxy group" is used herein to mean a straight-chain or branched alkynyloxy group including, for example, 2-propynyloxy group, 2-butynyloxy group, 3-butynyloxy group, or the like.

As the "$C_3$–$C_6$ cycloalkyloxy group", there can be mentioned, for example, a cyclopropyloxy group, cyclopentyloxy group, cyclohexyloxy group, or the like.

The term "$C_1$–$C_4$ haloalkoxy group" is used herein to mean a halogen-substituted straight-chain or branched alkoxy group including, for example, a fluoromethoxy group, difluoromethoxy group, trifluoromethoxy group, pentafluoroethoxy group, or the like.

The term "$C_1$–$C_6$ alkylthio group" is used herein to mean a straight-chain or branched alkylthio group including, for example, a methylthio group, ethylthio group, n-propylthio group, isopropylthio group, n-butylthio group, isobutylthio group, sec-butylthio group, tert-butylthio group, n-hexylthio group, or the like.

The term "$C_1$–$C_6$ alkylsulfinyl group" is used herein to mean a straight-chain or branched alkylsulfinyl group including, for example, a methylsulfinyl group, ethylsulfinyl group, n-propylsulfinyl group, isopropylsulfinyl group, n-butylsulfinyl group, isobutylsulfinyl group, sec-butylsulfinyl group, tert-butylsulfinyl group, n-hexylsulfinyl group, or the like.

The term "$C_1$–$C_6$ alkylsulfonyl group" is used herein to mean a straight-chain or branched alkylsulfonyl group including, for example, a methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-hexylsulfonyl group, or the like.

The term "$C_1$–$C_6$ alkylamino group" is used herein to mean a straight-chain or branched alkylamino group including, for example, a methylamino group, ethylamino group, n-propylamino group, isopropylamino group, n-butylamino group, isobutylamino group, sec-butylamino group, tert-butylamino group, ni-hexylamino group, or the like.

As the term "di($C_1$–$C_6$ alkyl)amino group", there can be mentioned, for example, a dimethylamino group, diethylamino group, dipropylamino group, dibutylamino group, or the like.

The term "($C_1$–$C_6$ alkyl)carbonyl group" is used herein to mean a straight-chain or branched alkylcarbonyl group including, for example, an acetyl group, propionyl group, butyryl group, isobutyryl group, or the like.

The term "($C_1$–$C_6$ alkoxy)carbonyl group" is used herein to mean a straight-chain or branched alkoxycarbonyl group including, for example, a methoxycarbonyl group, ethoxycarbonyl group, n-propoxycarbonyl group, isopropoxycarbonyl group, n-butoxycarbonyl group, isobutyloxycarbonyl group, sec-butoxycarbonyl group, tert-butoxycarbonyl group, n-pentyloxycarbonyl group, n-hexyloxycarbonyl group, or the like.

The term "hetrocyclyl group" is used herein to mean a saturated cyclyl group including at least one oxygen atom or sulfur atom as a constituent atom, including, for example, a 3-oxolanyl group, 4-oxanyl group, 3-thiolanyl group, 4-thianyl group, or the like.

The compounds represented by Formula (I) according to the present invention can exist as optical isomers by virtue of the presence of one or more asymmetric carbon atoms in a molecule. The present invention relates to all such diastereomers, enantiomers, and mixtures thereof.

The preferred compounds represented by Formula (I) according to the present invention are those in which:

$R^1$ represents a hydrogen atom, methyl group, cyclopropyl group, methylthio group, ethylthio group, alkylthio group, propargylthio group, methoxy group, ethoxy group, phenoxy group, or phenyl group, $R^2$ represents a methyl group, ethyl group, isopropyl group, trifluoromethyl group, chlorodifluoromethyl group, difluoromethyl group, dichloromethyl group, dibromornethyl group, methoxy group, methylthio group, or chlorine atom, $R^3$ represents a hydrogen atom, methyl group, ethyl group, chlorine atom, or bromine atom, $R^4$ represents a hydrogen atom, methyl group, or ethyl group, $R^5$ represents a hydrogen atom, methyl group, ethyl group, or n-propyl group, $R^6$ represents a methyl group, ethyl group, n-propyl group, isopropyl group, n-butyl group, isobutyl group, sec-butyl group, tert-butyl group, cyclopropyl group, cyclopentyl group, or dichloromethyl group, and Q represents a cyano group, acetyl group, propionyl group, methoxycarbonyl group, or ethoxycarbonyl group.

Next, representative examples of the compounds represented by Formula (I) according to the present invention are listed in Tables 1~15. However, it should be understood that the present invention is not limited to these compounds. Compound Numbers given in the Tables will be referred to in the subsequent description.

In the tables, "Me" means a methyl group, "Et" means an ethyl group, "n-Pr" means an n-propyl group, "i-Pr" means an isopropyl group, "n-Bu" means an n-butyl group, "i-Bu" means an isobutyl group, "s-Bu" means a sec-butyl group, "t-Bu" means a tert-butyl group, and "Ph" means a phenyl group. Therefore, for example "Ph(4-Cl)" means 4-chlorophenyl group. "Isomer A" represents an A-configurational diastereomer, "Isomer B" represents a B-configurational diastereomer, and "Isomer M" represents a mixture of an A-configurational diastereomer and a B-configurational diastereomer. "Isomer RA" represents an A-configurational diastereomer wherein the acid moiety is an optically active (R-configurational) one, "Isomer RB" represents a B-configurational diastereomer wherein the acid moiety is an optically active (R-configurational) one, and "Isomer RM" represents a mixture of the diastereomers wherein the acid moiety is an optically active (R-configurational) one. "Isomer SA" represents an A-configurational diastereomer wherein the acid moiety is an optically active (S-configurational) one, "Isomer SB"

represents a B-configurational diastereomer wherein the acid moiety is an optically active (S-configurational) one, and "Isomer SM" represents a mixture of the diastereomers wherein the acid moiety is an optically active (S-configurational) one. "A-configurational diastereomer" means a low-polar diastereomer separated by column chromatography on silica gel, high performance liquid chromatography, or the like, while "B-configurational diastereomer" means a high-polar diastereomer separated in the same manner as mentioned above.

TABLE 1

| Compound No. | $R^1$ | $R^2$ | $R^3$ | $R^4$ | $R^5$ | $R^6$ | Q | Melting Point (° C.) or Refractive Index ($n_D^{20}$) | Isomer |
|---|---|---|---|---|---|---|---|---|---|
| A-1 | H | Me | Cl | Me | Me | i-Pr | CN | 115~117 | M |
| A-2 | H | Me | Cl | Me | Me | Me | CN | | |
| A-3 | H | Et | $CF_3$ | H | Me | i-Pr | CN | | |
| A-4 | H | Et | F | Me | Me | i-Pr | CN | | |
| A-5 | H | Et | Cl | Me | Me | i-Pr | CN | 129~131 | M |
| A-6 | H | Et | Cl | Me | Et | Et | CN | 133~134 | |
| A-7 | H | Et | Cl | H | Me | i-Pr | CN | 1.5166 | |
| A-8 | H | Et | Cl | H | Me | $CH_2OMe$ | CN | | |
| A-9 | H | Et | Br | Me | Me | i-Pr | CN | | |
| A-10 | H | Et | I | Me | Me | i-Pr | CN | | |
| A-11 | H | Et | cyclopropyl | H | Me | i-Pr | CN | | |
| A-12 | H | Et | H | Me | Me | t-Bu | CN | 140~142 | M |
| A-13 | H | Et | Me | Me | Me | i-Pr | CN | 148~150 | M |
| A-14 | H | H | Cl | Me | Me | i-Pr | CN | | |
| A-15 | H | i-Pr | H | Me | Me | i-Pr | CN | 89~90 | M |
| A-16 | H | i-Pr | H | Me | Me | t-Bu | CN | 95~97 | M |
| A-17 | H | i-Pr | Cl | Me | H | i-Pr | CN | | |
| A-18 | H | i-Pr | Cl | Me | H | t-Bu | CN | 165~168 | M |
| A-19 | H | i-Pr | Cl | Me | H | i-Pr | COOMe | | |
| A-20 | H | i-Pr | Cl | Me | H | t-Bu | COOMe | | |
| A-21 | H | i-Pr | Cl | Me | Me | i-Pr | CN | 132~134 | M |
| A-22 | H | i-Pr | Cl | Me | Me | t-Bu | CN | 87~89 | M |
| A-23 | H | i-Pr | Cl | Me | s-Bu | Me | CN | | |
| A-24 | H | i-Pr | Cl | Me | cyclopropyl | cyclopropyl | CN | | |
| A-25 | H | i-Pr | Cl | Me | Me | i-Pr | COOMe | 1.4987 | M |
| A-26 | H | i-Pr | Cl | Me | Me | t-Bu | COOMe | 1.5029 | M |
| A-27 | H | n-Pr | Cl | Me | Me | i-Pr | CN | 108~110 | M |

TABLE 2

| Compound No. | $R^1$ | $R^2$ | $R^3$ | $R^4$ | $R^5$ | $R^6$ | Q | Melting Point (° C.) or Refractive Index ($n_D^{20}$) | Isomer |
|---|---|---|---|---|---|---|---|---|---|
| A-28 | H | n-Pr | Cl | Me | Et | Et | CN | 95~97 | |
| A-29 | H | cyclopropyl | Cl | H | Me | i-Pr | CN | | |
| A-30 | H | $CH=CH_2$ | Cl | H | Me | i-Pr | CN | | |
| A-31 | H | SMe | Cl | Me | Me | i-Pr | CN | 150~151 | M |
| A-32 | H | OMe | Cl | Me | Me | i-Pr | CN | 140~142 | M |
| A-33 | H | O-cyclopropyl | Cl | H | Me | i-Pr | CN | | |

TABLE 2-continued

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-34 | H | OCH₂CH=CH₂ | Cl | H | Me | i-Pr | CN | | |
| A-35 | H | OCH₂C≡CH | Cl | H | Me | i-Pr | CN | | |
| A-36 | H | Cl | Cl | Me | Me | i-Pr | CN | 128~131 | |
| A-37 | H | Cl | Cl | Me | Me | i-Pr | COOMe | | |
| A-38 | H | CF₃ | H | Me | Me | i-Pr | CN | 137~139 | M |
| A-39 | H | CF₃ | Me | Me | Me | i-Pr | CN | 149~151 | M |
| A-40 | H | CF₃ | Me | Me | Et | Et | CN | 149~151 | |
| A-41 | H | CF₃ | Me | Me | Me | t-Bu | CN | 150~153 | A |
| A-42 | H | CF₃ | Me | Me | Me | t-Bu | CN | 125~128 | B |
| A-43 | H | CF₃ | Me | Me | Me | CHCl₂ | CN | 185~188 | M |
| A-44 | H | CF₃ | Me | Me | Me |  | CN | 131~134 | M |
| A-45 | H | CF₃ | Me | Me | Me | 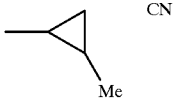 | CN | | |
| A-46 | H | CF₃ | Me | Me | Me | 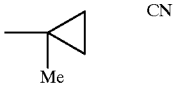 | CN | | |
| A-47 | H | CF₃ | Me | Me | Me | 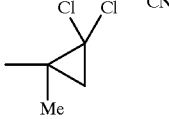 | CN | | |
| A-48 | H | CF₃ | Me | H | Me | i-Pr | COOMe | | |
| A-49 | H | CF₃ | Me | Me | Me | i-Pr | COOMe | 74~75 | M |
| A-50 | H | CF₃ | Me | Me | H | i-Pr | COOMe | | |
| A-51 | H | CF₃ | Me | CF₃ | H | i-Pr | COOMe | | |
| A-52 | H | CF₃ | Me | Me | H | i-Pr | COOCH₂CH=CH₂ | | |
| A-53 | H | CF₃ | Me | Me | H | t-Bu | CN | | |
| A-54 | H | CF₃ | Et | Me | Me | i-Pr | CN | 140~141 | A |
| A-55 | H | CF₃ | Et | Me | Me | i-Pr | CN | 149~150 | B |

TABLE 3

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-56 | H | CF₃ | Et | Me | Me | i-Pr | 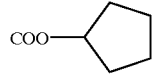 | | |
| A-57 | H | CF₃ | F | H | Me | i-Pr | CN | | |
| A-58 | H | CF₃ | Cl | H | Me | i-Pr | CN | 1.4871 | |
| A-59 | H | CF₃ | Cl | H | Me | t-Bu | CN | 156~157 | |
| A-60 | H | CF₃ | Cl | H | Et | Et | CN | | |
| A-61 | H | CF₃ | Cl | Me | Me | Me | CN | 148~151 | |
| A-62 | H | CF₃ | Cl | Me | Me | Et | CN | 141~144 | M |
| A-63 | H | CF₃ | Cl | Me | Me | n-Pr | CN | 106~109 | M |
| A-64 | H | CF₃ | Cl | Me | Me | i-Pr | CN | 157~159 | A |
| A-65 | H | CF₃ | Cl | Me | Me | i-Pr | CN | 126~129 | B |
| A-66 | H | CF₃ | Cl | Me | Me | i-Pr | CN | 149~150 | M |
| A-67 | H | CF₃ | Cl | Me | Me | 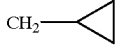 | CN | | |
| A-68 | H | CF₃ | Cl | Me | Me | 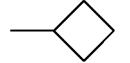 | CN | 124~125 | A |

TABLE 3-continued

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-69 | H | CF₃ | Cl | Me | Me | cyclobutyl | CN | 128~130 | B |
| A-70 | H | CF₃ | Cl | Me | Me | cyclobutyl | CN | 114~116 | M |
| A-71 | H | CF₃ | Cl | Me | Me | cyclopentyl | CN | 130~133 | A |
| A-72 | H | CF₃ | Cl | Me | Me | cyclopentyl | CN | 134~137 | B |
| A-73 | H | CF₃ | Cl | Me | Me | cyclopentyl | CN | 107~109 | M |
| A-74 | H | CF₃ | Cl | Me | Me | i-Bu | CN | 91~93 | M |
| A-75 | H | CF₃ | Cl | Me | Me | t-Bu | CN | 155~157 | A |
| A-76 | H | CF₃ | Cl | Me | Me | t-Bu | CN | 129~132 | B |
| A-77 | H | CF₃ | Cl | Me | Me | t-Bu | CN | 134~136 | M |
| A-78 | H | CF₃ | Cl | Me | Et | Et | CN | 153~154 | |
| A-79 | H | CF₃ | Cl | Me | cyclopropyl | cyclopropyl | CN | 125~128 | |
| A-80 | H | CF₃ | Cl | Me | | 1-methylcyclopentyl | CN | 172~174 | |
| A-81 | H | CF₃ | Cl | Me | | 1,2-dimethylcyclopentyl | CN | 170~172 | M |
| A-82 | H | CF₃ | Cl | Me | | 1,4-dimethylcyclohexyl | CN | 141~143 | |

TABLE 4

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-83 | H | CF₃ | Cl | Me | | 1,3,5-trimethylcyclohexyl | CN | 160~162 | |

TABLE 4-continued

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-84 | H | CF₃ | Cl | Me | | 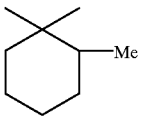 | CN | | |
| A-85 | H | CF₃ | Cl | Me | |  | CN | | |
| A-86 | H | CF₃ | Cl | Me | |  | COOMe | | |
| A-87 | H | CF₃ | Cl | Me | | 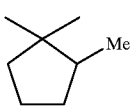 | COOMe | | |
| A-88 | H | CF₃ | Cl | Me | | 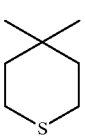 | CN | 214~216 | |
| A-89 | H | CF₃ | Cl | Me | | 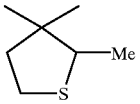 | CN | 180~183 | M |
| A-90 | H | CF₃ | Cl | Me | | 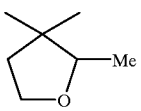 | CN | 174~177 | M |
| A-91 | H | CF₃ | Cl | Me | H | t-Bu | CN | 188~190 | M |
| A-92 | H | CF₃ | Cl | Me | H | s-Bu | CN | | |
| A-93 | H | CF₃ | Cl | Me | Me | i-Pr | COOMe | 85~86 | M |
| A-94 | H | CF₃ | Cl | Me | H | i-Pr | COOMe | 106~108 | M |
| A-95 | H | CF₃ | Cl | Me | Me | i-Pr | COOEt | 1.4765 | M |
| A-96 | H | CF₃ | Cl | Me | Me | i-Pr | COO-i-Pr | 1.4701 | M |
| A-97 | H | CF₃ | Cl | Me | Me | i-Pr | COOCH₂C≡CH | | |
| A-98 | H | CF₃ | Cl | Et | Me | i-Pr | CN | 154~156 | A |
| A-99 | H | CF₃ | Cl | Et | Me | i-Pr | CN | 116~118 | B |
| A-100 | H | CF₃ | Cl | Et | Me | i-Pr | CN | 139~142 | M |
| A-101 | H | CF₃ | Cl | Et | Me | t-Bu | CN | 106~109 | M |
| A-102 | H | CF₃ | Cl | Et | Me | s-Bu | CN | | |
| A-103 | H | CF₃ | Cl | n-Pr | Me | i-Pr | CN | | |

TABLE 5

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-104 | H | CH(Cl)Me | Cl | H | Me | i-Pr | CN | | |
| A-105 | H | CH(Cl)Me | Cl | Me | Me | i-Pr | CN | | |
| A-106 | H | CH(Cl)Me | Cl | Me | Me | t-Bu | CN | | |
| A-107 | H | CH(Cl)Me | Cl | Me | Me | i-Pr | COOMe | | |
| A-108 | H | CH(Cl)Me | Cl | Me | Me | t-Bu | COOMe | | |
| A-109 | H | CF₃ | Br | Me | Me | i-Pr | CN | 176~177 | A |
| A-110 | H | CF₃ | Br | Me | Me | i-Pr | CN | 163~164 | B |

TABLE 5-continued

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-111 | H | CF₃ | Br | Me | Me | i-Pr | CN | 153~154 | M |
| A-112 | H | CF₃ | Br | Me | Me | t-Bu | CN | 170~171 | A |
| A-113 | H | CF₃ | Br | Me | Me | t-Bu | CN | 168~170 | B |
| A-114 | H | CF₃ | Br | Me | Me | t-Bu | CN | 147~149 | M |
| A-115 | H | CF₃ | Br | Me | H | t-Bu | CN | | |
| A-116 | H | CF₃ | Br | Me | Me | i-Pr | COOMe | 110~111 | M |
| A-117 | H | CF₃ | I | Me | Me | i-Pr | CN | | |
| A-118 | H | CF₃ | CN | Me | Me | t-Bu | CN | | |
| A-119 | H | Ph | H | Me | Me | i-Pr | CN | | |
| A-120 | H | NHPr-i | H | Me | Me | i-Pr | CN | | |
| A-121 | H | N(Me)₂ | H | Me | Me | i-Pr | CN | | |
| A-122 | H | NHPr-i | Cl | Me | Me | i-Pr | CN | | |
| A-123 | H | N(Me)₂ | Cl | Me | Me | i-Pr | CN | | |
| A-124 | H | CF₃ | OMe | Me | Me | t-Bu | CN | | |
| A-125 | H | —CH=CH—CH=CH— | | Me | Me | i-Pr | CN | 139~141 | M |
| A-126 | H | —(CH₂)₄— | | Me | Me | t-Bu | CN | | |
| A-127 | H | —(CH₂)₃— | | Me | Me | t-Bu | CN | | |
| A-128 | cyclopropyl | CF₃ | Cl | Me | Me | i-Pr | CN | 131~132 | A |
| A-129 | cyclopropyl | CF₃ | Cl | Me | Me | i-Pr | CN | 128~130 | M |
| A-130 | cyclopropyl | CF₃ | Cl | Me | Et | i-Pr | CN | | |
| A-131 | Cl | OMe | H | Me | Me | i-Pr | CN | | |
| A-132 | Cl | SMe | H | Me | Me | i-Pr | CN | 1.5381 | M |
| A-133 | CF₃ | Me | Cl | Me | Me | i-Pr | CN | | |
| A-134 | CF₃ | Et | Me | Me | Me | i-Pr | CN | | |

TABLE 6

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-135 | Me | Me | NO₂ | Me | Me | i-Pr | CN | | |
| A-136 | Me | Et | i-Pr | Me | Me | i-Pr | CN | 140~143 | M |
| A-137 | Me | Et | i-Pr | Me | Me | t-Bu | CN | 1.5021 | M |
| A-138 | Me | C≡CMe | H | Me | Me | t-Bu | CN | | |
| A-139 | Me | CH=CHMe | H | Me | Me | i-Pr | CN | | |
| A-140 | Me | CH=C(Cl)Me | H | Me | Me | i-Pr | CN | | |
| A-141 | Me | CF₃ | H | Me | Me | i-Pr | CN | 111~113 | A |
| A-142 | Me | CF₃ | H | Me | Me | i-Pr | CN | 1.4672 | B |
| A-143 | Me | CF₃ | H | Me | Me | i-Pr | CN | 1.4710 | M |
| A-144 | Me | CF₃ | H | Me | Me | t-Bu | CN | 120~122 | A |
| A-145 | Me | CF₃ | H | Me | Me | t-Bu | CN | 135~137 | B |
| A-146 | Me | CF₃ | H | Me | Me | i-Pr | COOMe | | |
| A-147 | Me | CF₃ | Cl | H | Me | i-Pr | CN | | |
| A-148 | Me | CF₃ | Cl | Me | H | t-Bu | CN | | |
| A-149 | Me | CF₃ | Cl | Me | Me | i-Pr | CN | 130~132 | A |
| A-150 | Me | CF₃ | Cl | Me | Me | i-Pr | CN | 154~156 | B |
| A-151 | Me | CF₃ | Cl | Me | Me | t-Bu | CN | 133~134 | A |
| A-152 | Me | CF₃ | Cl | Me | Me | t-Bu | CN | 137~139 | B |
| A-153 | Me | CF₃ | Cl | Me | Et | Et | CN | 135~137 | |
| A-154 | Me | CF₃ | Cl | Me | cyclopropyl | cyclopropyl | CN | | |
| A-155 | Me | CF₃ | Cl | Me | Me | CH₂CH=CH₂ | COOEt | | |
| A-156 | Me | CF₃ | Cl | Me | | cyclopentyl | CN | 189~191 | |

TABLE 6-continued

| Compound No. | R$^1$ | R$^2$ | R$^3$ | R$^4$ | R$^5$ | R$^6$ | Q | Melting Point (° C.) or Refractive Index (n$_D^{20}$) | Isomer |
|---|---|---|---|---|---|---|---|---|---|
| A-157 | Me | CF$_3$ | Cl | Me | | (2,2-dimethylcyclopentyl, Me) | CN | 122~125 | M |
| A-158 | Me | CF$_3$ | Cl | Me | Me | i-Pr | COOMe | 122~125 | M |
| A-159 | Me | CF$_3$ | Cl | Me | Me | i-Pr | COOEt | 1.4778 | M |
| A-160 | Me | CF$_3$ | Cl | Et | Me | i-Pr | CN | | |
| A-161 | Me | CF$_3$ | Cl | (cyclopropyl) | Me | i-Pr | CN | | |
| A-162 | Me | Ph | H | Me | Me | i-Pr | CN | | |
| A-163 | Me | Ph(4-Cl) | H | Me | Me | i-Pr | CN | | |

TABLE 7

| Compound No. | R$^1$ | R$^2$ | R$^3$ | R$^4$ | R$^5$ | R$^6$ | Q | Melting Point (° C.) or Refractive Index (n$_D^{20}$) | Isomer |
|---|---|---|---|---|---|---|---|---|---|
| A-164 | Me | Ph(4-Me) | H | Me | Me | i-Pr | CN | | |
| A-165 | Me | Ph(4-OMe) | H | Me | Me | i-Pr | CN | | |
| A-166 | Me | CF$_3$ | Me | Me | Me | i-Pr | CN | 105~108 | A |
| A-167 | Me | CF$_3$ | Me | Me | Me | i-Pr | CN | 172~175 | B |
| A-168 | Me | CF$_3$ | Me | Me | Me | t-Bu | CN | 128~129 | A |
| A-169 | Me | CF$_3$ | Me | Me | Me | t-Bu | CN | 131~132 | B |
| A-170 | Me | CF$_3$ | Me | H | Me | i-Pr | CN | | |
| A-171 | Me | CF$_3$ | Me | H | Me | t-Bu | CN | | |
| A-172 | i-Pr | CF$_3$ | H | Me | Me | i-Pr | CN | 131~134 | M |
| A-173 | t-Bu | CF$_3$ | H | Me | Me | i-Pr | CN | | |
| A-174 | OCH$_2$C≡CH | Me | Cl | Me | Me | i-Pr | CN | | |
| A-175 | OCH$_2$CH=CH$_2$ | Me | Cl | Me | Me | i-Pr | CN | | |
| A-176 | OMe | CF$_3$ | Me | Me | Me | i-Pr | CN | not determined | M |
| A-177 | OMe | SMe | H | Me | Me | i-Pr | CN | not determined | M |
| A-178 | (O-cyclopropyl) | Me | Cl | Me | Me | i-Pr | CN | | |
| A-179 | NH-i-Pr | CF$_3$ | H | Me | Me | i-Pr | CN | | |
| A-180 | N(Me)$_2$ | CF$_3$ | H | Me | Me | i-Pr | CN | | |
| A-181 | Ph | Me | COMe | Me | Me | i-Pr | CN | | |
| A-182 | Ph | Me | COOMe | Me | Me | i-Pr | CN | | |
| A-183 | Ph | CF$_3$ | H | Me | Me | i-Pr | CN | 152~154 | M |
| A-184 | Ph | CF$_3$ | H | Me | Me | t-Bu | CN | 155~157 | M |
| A-185 | Ph | CF$_3$ | H | Me | Me | i-Pr | COOMe | | |
| A-186 | Ph(2-Cl) | CF$_3$ | H | Me | Me | i-Pr | CN | | |
| A-187 | Ph(3-CN) | CF$_3$ | H | Me | Me | i-Fr | CN | | |
| A-188 | Ph(3-Me) | CF$_3$ | H | Me | Me | i-Pr | CN | | |
| A-189 | Ph(3-NO$_2$) | CF$_3$ | H | Me | Me | i-Pr | CN | | |
| A-190 | Ph(4-CF$_3$) | CF$_3$ | H | Me | Me | i-Pr | CN | | |
| A-191 | Ph(4-OMe) | CF$_3$ | H | Me | Me | i-Pr | CN | | |
| A-192 | SMe | Me | H | Me | Me | i-Pr | CN | 106~108 | M |
| A-193 | SMe | Et | H | Me | Me | i-Pr | CN | 106~108 | M |
| A-194 | SMe | Et | H | Me | Me | t-Bu | CN | 108~110 | M |

TABLE 8

| Compound No. | R$^1$ | R$^2$ | R$^3$ | R$^4$ | R$^5$ | R$^6$ | Q | Melting Point (° C.) or Refractive Index (n$_D^{20}$) | Isomer |
|---|---|---|---|---|---|---|---|---|---|
| A-195 | SMe | Et | Me | Me | Me | i-Pr | CN | 105~107 | M |
| A-196 | SMe | Et | Me | Me | Me | t-Bu | CN | 1.5303 | M |
| A-197 | SMe | Et | Me | Me | Me | i-Pr | COMe | | |
| A-198 | SMe | Et | Me | Me | Me | i-Pr | COOMe | | |
| A-199 | SMe | Et | Et | Me | Me | i-Pr | CN | 136~138 | M |

TABLE 8-continued

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-200 | SMe | Et | Et | Me | Me | t-Bu | CN | 77~78 | M |
| A-201 | SMe | Et | i-Pr | Me | Me | i-Pr | CN | 134~136 | M |
| A-202 | SMe | Et | i-Pr | Me | Me | t-Bu | CN | 84~85 | M |
| A-203 | SMe | i-Pr | H | Me | Me | i-Pr | CN | 99~102 | M |
| A-204 | SMe | i-Pr | H | Me | Me | i-Pr | COOMe | 57~60 | M |
| A-205 | SMe | i-Pr | H | Me | Me | i-Pr | COOMe | 75~77 | B |
| A-206 | SMe | i-Pr | H | Me | 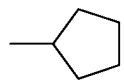 | Me | CN | | |
| A-207 | SMe | i-Pr | H | Me | 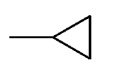 | 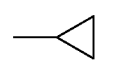 | CN | | |
| A-208 | SMe | i-Pr | Cl | Me | Me | i-Pr | CN | 120~122 | M |
| A-209 | SMe | i-Pr | Cl | Me | Me | t-Bu | CN | | |
| A-210 | SMe | i-Pr | Cl | Me | Me | i-Pr | COOMe | 41~43 | M |
| A-211 | SMe | i-Pr | Cl | Me | Et | i-Pr | CN | | |
| A-212 | SMe | i-Pr | Cl | Me | Et | Et | CN | | |
| A-213 | SMe | i-Pr | Cl | Me | 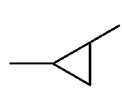 | 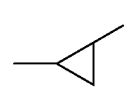 | CN | | |
| A-214 | SMe | n-Pr | H | Me | Me | i-Pr | CN | 130~132 | M |
| A-215 | SMe | n-Pr | H | Me | Me | t-Bu | CN | 95~97 | M |
| A-216 | SMe | C(Me)₂Cl | Cl | Me | Me | i-Pr | CN | 132~135 | M |
| A-217 | SMe | C(Me)₂Cl | Cl | Me | Me | t-Bu | CN | | |
| A-218 | SMe | C(Me)₂Cl | Cl | Me | Me | i-Pr | COOMe | | |
| A-219 | SMe | CF₃ | H | Me | Me | i-Pr | CN | 110~113 | M |
| A-220 | SMe | CF₃ | H | Me | Me | t-Bu | CN | 108~110 | M |
| A-221 | SMe | CF₃ | H | Me | Me | 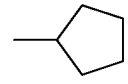 | CN | | |
| A-222 | SMe | CF₃ | H | H | Me | t-Bu | CN | | |
| A-223 | SMe | CF₃ | Cl | Me | Me | i-Pr | CN | 114~116 | M |
| A-224 | SMe | CF₃ | Cl | Me | Me | t-Bu | CN | 131~133 | M |
| A-225 | SMe | CF₃ | Cl | Me | Me | i-Pr | COOMe | 1.5093 | M |

TABLE 9

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-226 | SMe | CF₃ | Cl | Me | Me | t-Bu | COOMe | | |
| A-227 | SMe | CF₃ | Me | Me | Me | i-Pr | CN | 110~112 | M |
| A-228 | SMe | CF₃ | Me | Me | Me | t-Bu | CN | 78~80 | M |
| A-229 | SMe | CF₃ | Me | Me | Me | i-Pr | COOMe | not determined | M |
| A-230 | SMe | Cl | H | Me | Me | t-Bu | CN | | |
| A-231 | SMe | OMe | H | Me | Me | t-Bu | CN | | |
| A-232 | SMe | OCHF₂ | H | Me | Me | t-Bu | CN | | |
| A-233 | SMe | SCH₂C≡CH | H | Me | Me | t-Bu | CN | | |
| A-234 | SMe | SCH₂CH=CH₂ | H | Me | Me | t-Bu | CN | | |
| A-235 | SMe | SMe | H | Me | Me | t-Bu | CN | | |
| A-236 | SO₂Me | CF₃ | Me | Me | Me | i-Pr | CN | 68~70 | M |
| A-237 | SEt | Et | Et | Me | Me | i-Pr | CN | 97~99 | M |
| A-238 | SEt | Et | Et | Me | Me | t-Bu | CN | 64~66 | M |
| A-239 | SEt | Et | i-Pr | Me | Me | i-Pr | CN | 118~119 | M |
| A-240 | SEt | Et | i-Pr | Me | Me | t-Bu | CN | 107~108 | M |
| A-241 | SEt | CF₃ | H | Me | Me | i-Pr | CN | 104~105 | M |
| A-242 | SEt | CF₃ | H | Me | Me | t-Bu | CN | 88~90 | M |
| A-243 | SEt | CF₃ | H | Me | Me | i-Pr | COOMe | | |
| A-244 | SEt | CF₃ | H | Me | Me | t-Bu | COOMe | | |

TABLE 9-continued

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-245 | S—(cyclopropyl) | Me | Cl | Me | Me | i-Pr | CN | | |
| A-246 | S-i-Pr | Et | Et | Me | Me | i-Pr | CN | 72~74 | M |
| A-247 | S-i-Pr | Et | i-Pr | Me | Me | i-Pr | CN | 112~114 | M |
| A-248 | S-i-Pr | Et | i-Pr | Me | Me | t-Bu | CN | 99~100 | M |
| A-249 | S-i-Pr | CF₃ | H | Me | Me | i-Pr | CN | 69~71 | M |
| A-250 | S-i-Pr | CF₃ | H | Me | Me | t-Bu | CN | 108~110 | M |
| A-251 | SCH₂CH=CH₂ | CF₃ | H | Me | Me | i-Pr | CN | 96~98 | M |
| A-252 | SCH₂CH=CH₂ | CF₃ | H | Me | Me | t-Bu | CN | 96~98 | M |
| A-253 | SCH₂C≡CH | CF₃ | H | Me | Me | i-Pr | CN | 120~122 | M |
| A-254 | SCH₂C≡CH | CF₃ | H | Me | Me | t-Bu | CN | 107~109 | M |

TABLE 10

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-255 | H | CF₂Cl | Br | Me | Me | i-Pr | CN | 162~164 | M |
| A-256 | H | CF₂Cl | Br | Me | Me | t-Bu | CN | 141~142 | A |
| A-257 | H | CF₂Cl | Br | Me | Me | t-Bu | CN | 140~142 | B |
| A-258 | H | CF₂Cl | Br | Me | Me | t-Bu | CN | 121~124 | M |
| A-259 | H | CF₂Cl | Br | Me | Me | i-Pr | COMe | 156~159 | M |
| A-260 | H | CF₂Cl | Br | Me | Et | Et | COMe | 177~180 | |
| A-261 | H | CF₂Cl | Cl | Me | Me | i-Pr | CN | 165~166 | A |
| A-262 | H | CF₂Cl | Cl | Me | Me | i-Pr | CN | 165~167 | B |
| A-263 | H | CF₂Cl | Cl | Me | Me | i-Pr | CN | 158~160 | M |
| A-264 | H | CF₂Cl | Cl | Me | Me | t-Bu | CN | 134~136 | A |
| A-265 | H | CF₂Cl | Cl | Me | Me | t-Bu | CN | 118~120 | B |
| A-266 | H | CF₂Cl | Cl | Me | Me | t-Bu | CN | 111~114 | M |
| A-267 | H | CF₃ | Br | Me | Me | i-Pr | CN | 148~151 | RA |
| A-268 | H | CF₃ | Br | Me | Me | i-Pr | CN | 125~126 | RB |
| A-269 | H | CF₃ | Br | Me | Me | i-Pr | CN | 123~125 | RM |
| A-270 | H | CF₃ | Br | Me | Me | i-Pr | COMe | 143~144 | M |
| A-271 | H | CF₃ | Br | Me | Me | i-Pr | COEt | | |
| A-272 | H | CF₃ | Br | Me | Me | i-Pr | CO—(cyclopropyl) | | |
| A-273 | H | CF₃ | Br | Me | Me | i-Pr | COCF₃ | | |
| A-274 | H | CF₃ | Cl | Me | Et | i-Pr | CN | 138~141 | M |
| A-275 | H | CF₃ | Cl | Me | Me | (1-methylcyclopropyl) | CN | 113~114 | M |
| A-276 | H | CF₃ | Cl | Me | Me | t-Bu | CN | 117~118 | RA |
| A-277 | H | CF₃ | Cl | Me | Me | t-Bu | CN | 120~123 | RB |
| A-278 | H | CF₃ | Cl | Me | Me | t-Bu | CN | 115~116 | SA |
| A-279 | H | CF₃ | Cl | Me | Me | t-Bu | CN | 118~121 | SB |
| A-280 | H | CF₃ | Cl | Et | Me | t-Bu | CN | 123~124 | A |
| A-281 | H | CF₃ | Cl | Et | Me | t-Bu | CN | 106~109 | M |
| A-282 | H | CF₃ | Cl | Me | Me | i-Pr | CN | 155~158 | RA |
| A-283 | H | CF₃ | Cl | Me | Me | i-Pr | CN | 84~85 | RB |
| A-284 | H | CF₃ | Cl | Me | Me | i-Pr | CN | 111~114 | RM |
| A-285 | H | CF₃ | Cl | Me | Me | i-Pr | CN | 150~153 | SA |

TABLE 11

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-286 | H | CF₃ | Cl | Me | Me | i-Pr | CN | 94~96 | SB |
| A-287 | H | CF₃ | Cl | Me | Me | i-Pr | CN | 104~106 | SM |
| A-288 | H | CF₃ | Cl | Me | Me | i-Pr | COMe | 151~154 | M |

TABLE 11-continued

| Compound No. | $R^1$ | $R^2$ | $R^3$ | $R^4$ | $R^5$ | $R^6$ | Q | Melting Point (° C.) or Refractive Index ($n_D^{20}$) | Isomer |
|---|---|---|---|---|---|---|---|---|---|
| A-289 | H | CF$_3$ | Cl | Me | Me | i-Pr | COPr-n | | |
| A-290 | H | CF$_3$ | Cl | Me | Me | i-Pr | COCH$_2$Cl | | |
| A-291 | H | CF$_3$ | Cl | Me | Et | Et | COMe | 170~172 | |
| A-292 | H | CF$_3$ | Cl | Me | Me | Et | COMe | 178~181 | M |
| A-293 | H | CF$_3$ | Cl | Me | Me | Me | COMe | 201~203 | |
| A-294 | H | CF$_3$ | Me | Me | Me | t-Bu | CN | 108~110 | RA |
| A-295 | H | CF$_3$ | Me | Me | Me | t-Bu | CN | 109~112 | RB |
| A-296 | H | CF$_3$ | Me | Me | Me | i-Pr | COMe | 120~123 | M |
| A-297 | H | CF$_3$ | Me | Me | Me | Et | COMe | 155~158 | M |
| A-298 | H | CF$_3$ | Me | Me | Et | Et | COMe | 141~144 | |
| A-299 | Me | CF$_3$ | Me | Me | Me | i-Pr | COMe | 114~117 | M |
| A-300 | Me | CF$_3$ | Me | Me | Me | Et | COMe | 138~141 | M |
| A-301 | Me | CF$_3$ | Me | Me | Et | Et | COMe | 95~98 | |
| A-302 | H | CHBr$_2$ | Cl | Me | Me | i-Pr | CN | 54~57 | M |
| A-303 | H | CHBr$_2$ | Cl | Me | Me | t-Bu | CN | 155~158 | M |
| A-304 | H | CHCl$_2$ | Cl | Me | Me | i-Pr | CN | 160~162 | M |
| A-305 | H | CHCl$_2$ | Cl | Me | Me | t-Bu | CN | 152~154 | M |
| A-306 | H | CHF$_2$ | Br | Me | Me | i-Pr | CN | 166~167 | A |
| A-307 | H | CHF$_2$ | Br | Me | Me | i-Pr | CN | 147~148 | B |
| A-308 | H | CHF$_2$ | Br | Me | Me | i-Pr | CN | 154~155 | M |
| A-309 | H | CHF$_2$ | Br | Me | Me | t-Bu | CN | 138~141 | A |
| A-310 | H | CHF$_2$ | Br | Me | Me | t-Bu | CN | 128~129 | B |
| A-311 | H | CHF$_2$ | Br | Me | Me | t-Bu | CN | 111~113 | M |
| A-312 | H | CHF$_2$ | Cl | Me | Me | i-Pr | CN | 171~172 | A |
| A-313 | H | CHF$_2$ | Cl | Me | Me | i-Pr | CN | 141~144 | B |
| A-314 | H | CHF$_2$ | Cl | Me | Me | i-Pr | CN | 152~155 | M |
| A-315 | H | CHF$_2$ | Cl | Me | Me | t-Bu | CN | 125~127 | A |
| A-316 | H | CHF$_2$ | Cl | Me | Me | t-Bu | CN | 119~122 | B |

TABLE 12

| Compound No. | $R^1$ | $R^2$ | $R^3$ | $R^4$ | $R^5$ | $R^6$ | Q | Melting Point (° C.) or Refractive Index ($n_D^{20}$) | Isomer |
|---|---|---|---|---|---|---|---|---|---|
| A-317 | H | CHF$_2$ | Cl | Me | Me | t-Bu | CN | 94~97 | M |
| A-318 | H | CHF$_2$ | Cl | Me | Me | i-Pr | COMe | 159~162 | M |
| A-319 | H | Ph | Cl | Me | Me | i-Pr | CN | 40~42 | M |
| A-320 | H | Ph | Cl | Me | Me | t-Bu | CN | 1.5401 | M |
| A-321 | H | t-Bu | Br | Me | Me | i-Pr | CN | 151~153 | M |
| A-322 | H | t-Bu | Br | Me | Me | t-Bu | CN | 126~129 | M |
| A-323 | Me | CF$_3$ | Br | Me | Me | i-Pr | CN | 147~149 | A |
| A-324 | Me | CF$_3$ | Br | Me | Me | i-Pr | CN | 141~143 | B |
| A-325 | Me | CF$_3$ | Br | Me | Me | i-Pr | CN | 136~137 | M |
| A-326 | Me | CF$_3$ | Br | Me | Me | t-Bu | CN | 124~125 | A |
| A-327 | Me | CF$_3$ | Br | Me | Me | t-Bu | CN | 142~145 | B |
| A-328 | Me | CF$_3$ | Br | Me | Me | t-Bu | CN | 142~144 | M |
| A-329 | Me | CF$_3$ | Br | Me | Me | t-Bu | COMe | | |
| A-330 | Me | CF$_3$ | Br | Me | Me | i-Pr | COMe | 122~124 | M |
| A-331 | Me | CF$_3$ | Br | Me | Me | i-Pr |  | | |
| A-332 | Me | CF$_3$ | Br | Me | Me | i-Pr | COEt | | |
| A-333 | Me | CF$_3$ | Br | Me | Et | Et | COMe | 132~134 | |
| A-334 | Me | CF$_3$ | Cl | Me | Me | i-Pr | COMe | 124~126 | M |
| A-335 | Me | CF$_3$ | Cl | Me | Me | Et | COMe | 131~134 | M |
| A-336 | Et | CF$_3$ | Br | Me | Me | i-Pr | CN | 105~108 | M |
| A-337 | Et | CF$_3$ | H | Me | Me | i-Pr | CN | 90~93 | M |
| A-338 | i-Pr | CF$_3$ | Br | Me | Me | i-Pr | CN | 131~133 | M |
| A-339 | i-Pr | CF$_3$ | Br | Me | Me | t-Bu | CN | 150~151 | M |
| A-340 | i-Pr | CF$_3$ | H | Me | Me | i-Pr | CN | 131~134 | M |
| A-341 | i-Pr | CF$_3$ | H | Me | Me | t-Bu | CN | 129~132 | M |
| A-342 | OMe | CF$_3$ | Br | Me | Me | i-Pr | CN | 126~129 | M |
| A-343 | OMe | CF$_3$ | Br | Me | Me | t-Bu | CN | 118~119 | A |
| A-344 | OMe | CF$_3$ | Br | Me | Me | t-Bu | CN | 108~110 | B |
| A-345 | OMe | CF$_3$ | Br | Me | Me | t-Bu | CN | 112~115 | M |
| A-346 | OEt | CF$_3$ | Br | Me | Me | i-Pr | CN | 111~113 | M |
| A-347 | OEt | CF$_3$ | Br | Me | Me | t-Bu | CN | 97~98 | M |

TABLE 13

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| A-348 | OPh | CF₃ | Br | Me | Me | t-Bu | CN | 193~194 | M |
| A-349 | OPh | CF₃ | Cl | Me | Me | i-Pr | CN | 162~165 | M |
| A-350 | OPh | CF₃ | H | Ne | Me | i-Pr | CN | 155~158 | M |
| A-351 | OPh(2-Cl) | CF₃ | H | Me | Me | i-Pr | CN | | |
| A-352 | OPh(3-Me) | CF₃ | H | Me | Me | i-Pr | CN | | |
| A-353 | OPh(4-OMe) | CF₃ | H | Me | Me | i-Pr | CN | | |
| A-354 | OPh | CF₃ | Br | Me | Me | i-Pr | CN | 170~173 | M |
| A-355 | Ph | CF₃ | Cl | Me | Me | i-Pr | CN | 152~155 | M |
| A-356 | Ph | CF₃ | Cl | Me | Me | t-Bu | CN | 166~169 | M |
| A-357 | OPh(2-CN) | CF₃ | H | Me | Me | i-Pr | CN | | |
| A-358 | OPh(3-NO₂) | CF₃ | H | Me | Me | i-Pr | CN | | |
| A-359 | OPh(4-CF₃) | CF₃ | H | Me | Me | i-Pr | CN | | |
| A-360 | SMe | CF₃ | Br | Me | Me | i-Pr | CN | 129~130 | M |
| A-361 | SMe | CF₃ | Br | Me | Me | t-Bu | CN | 139~142 | M |
| A-362 | SO₂Me | CF₃ | Br | Me | Me | i-Pr | CN | 75~78 | M |
| A-363 | SMe | CF₃ | Br | Me | Me | Me | CO-cyclopropyl-F | | |
| A-364 | SMe | CF₃ | Br | Me | Me | Me | CO-cyclopropyl-Me | | |

TABLE 14

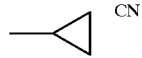

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| B-1 | H | CF₃ | Br | Me | Me | i-Pr | CN | 139~141 | M |
| B-2 | H | CF₃ | Br | Me | Me | t-Bu | CN | 158~159 | A |
| B-3 | H | CF₃ | Br | Me | Me | t-Bu | CN | 146~147 | B |
| B-4 | H | CF₃ | Br | Me | Me | t-Bu | COOMe | | |
| B-5 | H | CF₃ | Cl | Me | Me | i-Pr | CN | 1.5065 | A |
| B-6 | H | CF₃ | Cl | Me | Me | i-Pr | CN | 1.5107 | B |
| B-7 | H | CF₃ | Cl | Me | Me | i-Pr | CN | 1.5072 | M |
| B-8 | H | CF₃ | Cl | Me | Et | Et | CN | | |
| B-9 | H | CF₃ | Cl | Me | Me | i-Pr | COOMe | | |
| B-10 | H | CF₃ | Me | Me | Me | i-Pr | CN | 115~116 | A |
| B-11 | H | CF₃ | Me | Me | Me | i-Pr | CN | 110~112 | B |
| B-12 | H | CF₃ | Me | Me | Et | Et | CN | | |
| B-13 | H | CF₃ | Me | Me | Me | CHCl₂ | CN | | |
| B-14 | H | CF₃ | Me | Me | Me | t-Bu | CN | 143~145 | A |
| B-15 | H | CF₃ | Me | Me | Me | t-Bu | CN | 126~128 | B |
| B-16 | H | CF₃ | Me | Me | Me | cyclopropyl | CN | | |
| B-17 | H | i-Pr | Cl | Me | Me | i-Pr | CN | 73~75 | M |
| B-18 | H | i-Pr | Cl | Me | Me | t-Bu | CN | 1.5339 | M |
| B-19 | H | i-Pr | Cl | Me | H | i-Pr | CN | | |
| B-20 | H | i-Pr | Cl | Me | H | t-Bu | CN | | |
| B-21 | H | i-Pr | H | Me | Me | i-Pr | CN | 1.5305 | M |
| B-22 | H | i-Pr | H | Me | Me | t-Bu | CN | 1.5305 | M |

TABLE 15

| Compound No. | R¹ | R² | R³ | R⁴ | R⁵ | R⁶ | Q | Melting Point (° C.) or Refractive Index ($n_D^{20}$) | Isomer |
|---|---|---|---|---|---|---|---|---|---|
| B-23 | Me | CF₃ | H | Me | Me | i-Pr | CN | | |
| B-24 | Me | CF₃ | H | Me | Me | t-Bu | CN | | |
| B-25 | cyclopropyl | CF₃ | Cl | Me | Me | i-Pr | CN | not determined | A |
| B-26 | cyclopropyl | CF₃ | Cl | Me | Me | i-Pr | CN | 117~119 | B |
| B-27 | cyclopropyl | CF₃ | Cl | Me | H | i-Pr | COOMe | | |
| B-28 | SMe | CF₃ | Cl | Me | Me | i-Pr | CN | 102~104 | M |
| B-29 | SMe | CF₃ | Cl | Me | Me | t-Bu | CN | 132~134 | M |
| B-30 | SMe | Ph | H | Me | Me | i-Pr | CN | | |
| B-31 | SOMe | Ph | H | Me | Me | i-Pr | CN | | |
| B-32 | SO₂Me | Ph | H | Me | Me | i-Pr | CN | | |
| B-33 | Me | Ph(2-CN) | H | Me | Me | i-Pr | CN | | |
| B-34 | Me | Ph(3-CF₃) | H | Me | Me | i-Pr | CN | | |
| B-35 | Me | Ph(4-NO₂) | H | Me | Me | i-Pr | CN | | |

The compounds represented by Formula (I) can be synthesized according to, for example, the preparation processes shown below.

Preparation Process 1

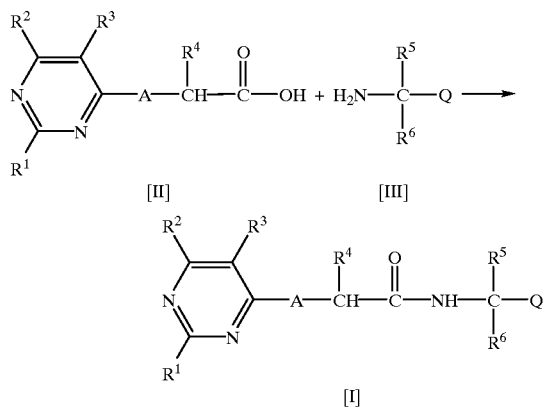

(wherein R¹, R², R³, R⁴, R⁵, R⁶, Q, and A have the same meanings as defined above).

The compounds of Formula (I) according to the present invention may be prepared by the reaction of pyrimidinyloxyalkanoic acid derivatives represented by Formula (II) with amines represented by Formula (III) using a condensing agent, in the presence of a catalyst and/or a base, if necessary. The present reaction is generally carried out in a solvent: this solvent can be any solvent that does not hinder the reaction, for example, hydrocarbons such as pentane, hexane, heptane, cyclohexane, petroleum ether, ligroin, benzene, toluene, xylene and the like, halogenated hydrocarbons such as dichloromethane, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, esters such as methyl acetate, ethyl acetate and the like, nitriles such as acetonitrile, propionitrile, and the like, aprotic polar solvents such as dimethylsulfoxide, N,N-dimethylformamide, sulfolane, and the like, and mixtures of solvents combining solvents selected from the aforementioned.

As the condensing agent, there can be mentioned 1-ethyl-3-(3-dimethylaminopropyl)carbodiimide hydrochloride, N,N'-dicyclohexylcarbodiimide, carbonyldiimidazole, 2-chloro-1,3-dimethylimidazolium chloride, or the like.

As the catalyst, there can be mentioned, for example, 4-dimethylaminopyridine, 1-hydroxybenzotriazole, dimethylformamide or the like.

The base can be any type of base generally used in this type of reaction. For example, there can be mentioned hydroxides of alkaline metals such as sodium hydroxide, potassium hydroxide and the like, hydroxides of alkaline earth metals such as calcium hydroxide and the like, carbonates of alkaline metals such as sodium carbonate, potassium carbonate and the like, organic bases such as triethylamine, trimethylamine, N,N-dimethylaniline, pyridine, N-methylpiperidine, 1,5-diazabicyclo[4.3.0]non-5-ene (DBN), 1,8-diazabicyclo[5.4.0]undec-7-ene (DBU), and the like, and preferably tertially amines such as triethylamine, pyridine, N-methylpiperidine and the like.

The present reaction is carried out at a temperature in a range from -50° C. to 150° C., and preferably in a range of from 0° C. to 60° C. The reaction time is preferably in a range from 1 to 30 hours.

Next, the synthesis process for each starting material will be explained.

The compounds represented by Formula (II) can be synthesized according to, for example, the preparation processes shown below.

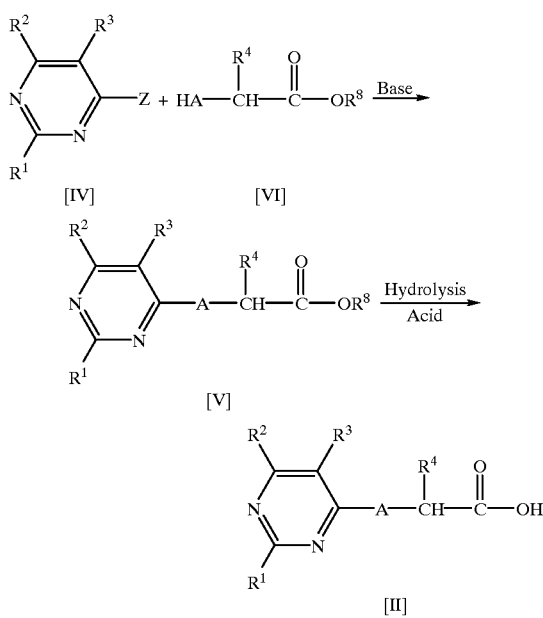

wherein $R^1$, $R^2$, $R^3$, $R^4$, and A have the same meanings as defined above, $R^8$ represents $C_1$ to $C_6$ alkyl group, and Z represents a leaving group such as a halogen atom, or the like).

The pyrimidinyloxyalkanoic acid derivatives represented by Formula (II) can be prepared, for example, by reacting pyrimidine derivatives represented by Formula (IV) with ester derivatives of alkanoic acids represented by Formula (VI) in the presence of a base to produce ester derivatives of pyrimidinyloxyalkanoic acids represented by Formula (V), and subsequently hydrolyzing the ester derivatives of pyrimidinyloxyalkanoic acids.

In the reaction schemes described above, the reaction of pyrimidine derivatives represented by Formula (IV) with ester derivatives represented by Formula (VI) is generally carried out in a solvent: this solvent can be any solvent that does not hinder the reaction, for example, hydrocarbons such as pentane, hexane, heptane, cyclohexane, petroleum ether, ligroin, benzene, toluene, xylene and the like, halogenated hydrocarbons such as dichloromethane, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, acetates such as methyl acetate, ethyl acetate and the like, nitriles such as acetonitrile, propionitrile, and the like, aprotic polar solvents such as dimethylsulfoxide, N,N-dimethylformamide, sulfolane, and the like, and mixture of solvents combining solvents selected from the aforementioned.

The base can be any type of base generally used in this type of reaction. For example, there can be mentioned inorganic bases such as sodium hydroxide, potassium hydroxide, sodium carbonate, potassium carbonate, sodium bicarbonate, sodium hydride, potassium hydride, and the like, or organic bases such as triethylamine, trimethylamine, N,N-dimethylaniline, pyridine, and the like.

The present reaction is carried out at a temperature in a range from −50° C. to 150° C., and preferably in a range of from 0° C. to 60° C. The reaction time is preferably in a range from 1 to 30 hours.

The reaction for obtaining pyrimidinyloxyalkanoic acid derivatives represented by Formula (II) by hydrolysis of ester derivatives of pyrimidinyloxyalkanoic acids represented by Formula (V) is generally carried out in a solvent: this solvent can be any solvent that does not hinder the reaction, for example, water, alcohols such as methanol, ethanol, 2-propanol, and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, and mixtures of solvents combining solvents selected from the aforementioned.

The base can be any type of base generally used in this type of reaction. For example, there can be mentioned inorganic bases such as sodium hydroxide, potassium hydroxide and the like.

The present reaction is carried out at a temperature in a range from −50° C. to 150° C., and preferably in a range of from 0° C. to 60° C. The reaction time is preferably in a range from 1 to 30 hours.

The compounds represented by Formula (IV) can be synthesized, for example, according to the known methods such as chlorination of hydroxypyrimidines using phosphorus oxychloride (see *Tetrahedron*, Vol. 35, p. 2087, 1979; or *Journal of Heterocyclic Chemistry*, Vol. 20, p. 219, 1983).

The compounds represented by Formula (III) can be produced, for example, using ketones, sodium cyanide, and ammonium chloride, according to the Strecker Method, which has been disclosed in *Organic Syntheses*, Vol. 3, p. 88, 1955; *Journal of Medicinal Chemistry*, Vol. 9, p. 911, 1966; or *Tetrahedron Letters*, Vol. 17, p. 1455. 1977.

Preparation Process 2

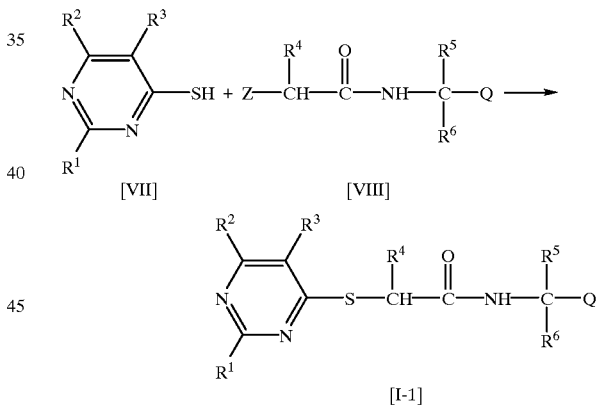

(wherein $R^1$, $R^2$, $R^3$, $R^4$, $R^5$, $R^6$, Q, and Z have the same meanings as defined above).

The compounds represented by Formula (I-1) according to the present invention can be prepared by the reaction of pyrimidine derivatives represented by Formula (VII) with alkanamide derivatives represented by Formula (VIII) in the presence of a base. The present reaction can be carried out in a solvent: this solvent can be the same solvent as described in Preparation Process 1, that does not hinder the reaction.

The base can be any type of base generally used in this type of reaction. For example, there can be mentioned inorganic bases such as sodium hydroxide, potassium hydroxide, sodium carbonate, potassium carbonate, sodium bicarbonate, sodium hydride, potassium hydride, and the like, or organic bases such as triethylamine, trimethylamine, N,N-dimethylaniline, pyridine, and the like.

The present reaction is carried out at a temperature of −50° C. to 150° C., and preferably 0° C. to 60° C. The reaction time is preferably in the range from 1 to 30 hours.

In the present reaction, the compounds represented by Formula (VII) can be produced, for example, according to the reaction of pyrimidine derivatives represented by Formula (IV) with thioureas.

In addition, the compounds represented by Formula (VIII) can be produced, for example, according to the reaction of halogenated alkanoyl halides with amine derivatives represented by Formula (III).

Preparation Process 3

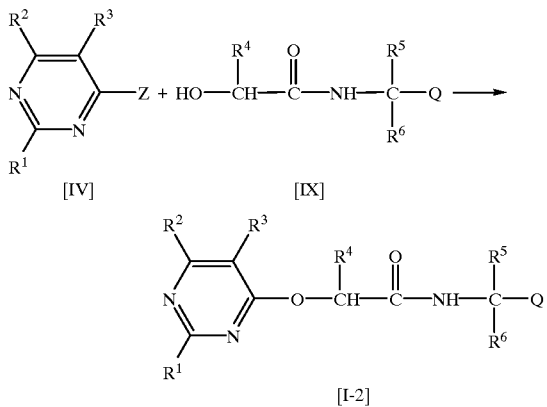

(wherein $R^1$, $R^2$, $R^3$, $R^4$, $R^5$, $R^6$, Q, and Z have the same meanings as defined above).

The compounds represented by Formula (I-2) according to the present invention can be prepared by the reaction of pyrimidine derivatives represented by Formula (IV) with alkanamide derivatives represented by Formula (IX) in the presence of a base. The present reaction can be carried out in a solvent which may be the same solvent as described in Preparation Process 1, that does not hinder the reaction.

As the base, there can be employed the same base as described in Preparation Process 2.

The present reaction is carried out at a temperature of −50° C. to 150° C., and preferably 0° C. to 60° C. The reaction time is preferably in the range from 1 to 30 hours.

In the present reaction, the compounds represented by Formula (IX) can be produced, for example, according to the deacylation of acetoxyalkanamide derivatives produced by the reaction of halogenated alkanamide derivatives represented by Formula (VIII) with sodium acetate.

BEST MODE FOR CARRYING OUT THE INVENTION

In the following, preparation examples of the compounds according to the present invention are provided.

PREPARATION EXAMPLE 1

Synthesis of 2-(5-chloro-6-etliylpyrimidin-4-yloxy)-N-(1-cyano-1,2-dimethylpropyl)acetamide (Compound No. A-7)

1-Ethyl-3-(3-dimethylaminopropyl)carbodiimide hydrochloride (1.1 g) was added to a solution containing 2-(5-chloro-6-ethylpyrimidin-4-yloxy)acetic acid (1.0 g) dissolved in methylene chloride (50 ml), at room temperature, and the mixture was stirred for 10 min. Subsequently, 2-amino-2,3-dimethylbutyronitrile (0.5 g) was added to the mixture, and the reaction mixture was stirred for 3 hours at room temperature. After completion of the reaction, water was added to the resulting mixture and the methylene chloride layer was washed with water, and subsequently dried over anhydrous magnesium sulfate. The methylene chloride was removed under reduced pressure. The residue was purified by column chromatography on silica gel to give 0.8 g of the desired compound having a refractive index of 1.5166 (20° C.).

Reference Example 1-a

Synthesis of ethyl 2-(5-chloro-6-ethylpyrimidi n-4-yloxy) acetate

60% Sodium hydride (0.5 g) was washed with hexane and then suspended in tetrahydrofuran (50 ml). Ethyl glycolate (1.2 g) was added to the suspension in a dropwise manner in an ice-cooled bath, and subsequently the mixture was stirred for an hour at room temperature. Subsequently, 4,5-dichloro-6-ethylpyrimidine (2.0 g) was added thereto in a dropwise manner, and the reaction mixture was stirred for 3 hours at room temperature. After completion of the reaction, water was added to the reaction liquid. The organic layer was extracted with ethyl acetate and then was dried over anhydrous magnesium sulfate. The ethyl acetate was removed under reduced pressure. The residue was purified by column chromatography on silica gel to give 2.6 g of the desired product as an oil.

Reference Example 1-b

Synthesis of 2-(5-chloro-6-ethylpyri midi n-4-yloxy) acetic acid (Intermediate Compound No. 2)

Ethyl 2-(5-chloro-6-ethylpyrimidin-4-yloxy)acetate (2.6 g) was dissolved in ethanol (50 ml). A solution containing sodium hydroxide (0.7 g) dissolved in water (10 ml) was added thereto in a dropwise manner, and subsequently the mixture was stirred for an hour at room temperature. After completion of the reaction, water was added to the reaction liquid. Subsequently, the reaction liquid was acidified using citric acid. The organic layer was extracted with ethyl acetate and then was dried over anhydrous magnesium sulfate. The ethyl acetate was removed under reduced pressure. The obtained crystals were washed with hexane to give 1.4 g of the desired product having a melting point of 158° C. to 159° C.

Table 16 shows physical properties of pyrimidinyloxyalkanoic acids that are intermediate compounds of the compounds according to the present invention, which are obtained in a manner similar to those described in Reference Example 1-a and Reference Example 1-b.

TABLE 16

| Intermediate Compound No. | $R^1$ | $R^2$ | $R^3$ | $R^4$ | Melting Point (° C.) |
|---|---|---|---|---|---|
| 1 | H | Me | Cl | Me | 143–145 |
| 2 | H | Et | Cl | H | 158–159 |
| 3 | H | Et | Cl | Me | 126–128 |

TABLE 16-continued $$\begin{array}{c} R^2 \quad R^3 \\ \diagdown \diagup \\ N \diagup \diagdown \diagup R^4 \quad O \\ \| \quad \| \\ -O-CH-C-OH \\ \diagup \diagdown N \diagup \\ R^1 \end{array}$$

| Intermediate Compound No. | R¹ | R² | R³ | R⁴ | Melting Point (° C.) |
|---|---|---|---|---|---|
| 4 | H | i-Pr | Cl | Me | 140~143 |
| 5 | H | CF₃ | Cl | H | 138~140 |
| 6 | H | CF₃ | Cl | Me | 112~113 |
| 7 | H | CF₃ | Cl | Et | 122~125 |
| 8 | H | CF₃ | Br | Me | 131~134 |
| 9 | H | CF₃ | Me | Me | 113~115 |
| 10 | Me | CF₃ | Cl | Me | 119~122 |
| 11 | SMe | Me | H | Me | 125~127 |
| 12 | SMe | Et | H | Me | 62~64 |
| 13 | SMe | n-Pr | H | Me | 56~58 |
| 14 | SMe | i-Pr | Cl | Me | 136~139 |
| 15 | SMe | CF₃ | H | Me | 90~93 |
| 16 | SMe | CF₃ | Cl | Me | 143~146 |
| 17 | SMe | CF₃ | Me | Me | 112~114 |
| 18 | Cl | SMe | H | Me | 137~139 |
| 19 | Me | CF₃ | Br | Me | 132~135 |
| 20 | Me | CF₃ | Me | Me | 102~104 |

PREPARATION EXAMPLE 2

Synthesis of methyl 2-(1-(5-chloro-6-trifluoromethylpyrimidin-4-yloxy)ethylcarbonylamino)-2,3-dimethylbutyrate (Compound No. A-93)

1-Ethyl-3-(3-dimethylaminopropyl)carbodiimide hydrochloride (1.1 g) was added to a solution containing 2-(5-chloro-6-trifluoromethylpyrimidin-4-yloxy)propionic acid (1.4 g) dissolved in methylene chloride (20 ml), at room temperature, and the mixture was stirred for 10 min. Subsequently, methyl 2-amino-2,3-dimethylbutyrate (0.8 g) was added to the mixture, and the reaction mixture was stirred for 4 hours at room temperature. After completion of the reaction, water was added to the resulting mixture and the methylene chloride layer was washed with water, and subsequently dried over anhydrous magnesium sulfate. The methylene chloride was removed under reduced pressure. The residue was purified by column chromatography on silica gel to give 1.3 g of the desired compound having a melting point of 85° C. to 86° C.

Reference Example 2-a

Synthesis of ethyl 2-(5-chloro-6-trifluoromethylpyrimidin-4-yloxy)propionate

60% Sodium hydride (0.6 g) was washed with hexane and then suspended in tetrahydrofuran (50 ml). Ethyl lactate (2.0 g) was added to the suspension in a dropwise manner in an ice-cooled bath, and subsequently the mixture was stirred for an hour at room temperature. Subsequently, 4,5-dichloro-6-trifluoromethylpyrimidine (3.1 g) was added thereto in a dropwise manner in an ice-cooled bath, and the reaction mixture was stirred for 3 hours at room temperature. After completion of the reaction, water was added to the reaction liquid. The organic layer was extracted with ethyl acetate and then was dried over anhydrous magnesium sulfate. The ethyl acetate was removed under reduced pressure. The residue was purified by column chromatography on silica gel to give 3.5 g of the desired product as an oil.

Reference Example 2-b

Synthesis of 2-(5-chloro-6-trifluoromethylpyrimidin-4-yloxy)propionic acid (Intermediate Compound No. 6)

Ethyl 2-(5-chloro-6-trifluoromethylpyrimidin-4-yloxy)propionate (3.5 g) was dissolved in 1,4-dioxane (20 ml). A solution containing sodium hydroxide (0.8 g) dissolved in water (10 ml) was added thereto in a dropwise manner in an ice-cooled bath, and subsequently the mixture was stirred for an hour at room temperature. After completion of the reaction, water was added to the reaction liquid. Subsequently, the reaction liquid was acidified using citric acid. The organic layer was extracted with ethyl acetate and then was dried over anhydrous magnesium sulfate. The ethyl acetate was removed under reduced pressure. The obtained crystals were washed with hexane to give 2.3 g of the desired product having a melting point of 112° C. to 113° C.

PREPARATION EXAMPLE 3

Synthesis of 2-(5-chloro-6-trifluoromethylpyrimidin-4-yloxy)-N-(1-cyanocyclopentyl)propionamide (Compound No. A-80)

1-Ethyl-3-(3-dimethylaminopropyl)carbodiimide hydrochloride (1.1 g) was added to a solution containing 2-(5-chloro-6-trifluoromethylpyrimidin-4-yloxy)propionic acid (1.0 g) dissolved in chloroform (30 ml), at room temperature, and the mixture was stirred for 30 min. Subsequently, 1-amino-cyclopentanecarbonitrile (0.4 g) was added to the mixture, and the reaction mixture was stirred for 10 hours at room temperature. After completion of the reaction, water was added to the resulting mixture and the chloroform layer was washed with water, and subsequently dried over anhydrous magnesium sulfate. The chloroform was removed under reduced pressure. The residue was purified by column chromatography on silica gel to give 0.6 g of the desired compound having a melting point of 172° C. to 174° C.

PREPARATION EXAMPLE 4

Synthesis of 2-(5-chloro-2-methyl-6-trifluoromethylpyrimidin-4-yloxy)-N-(1-cyano-1,2,2-trimethylpropyl)propionamide (Compound Nos. A-151 and A-152)

1-Ethyl-3-(3-dimethylaminopropyl)carbodiimide hydrochloride (0.8 g) was added to a solution containing 2-(5-chloro-2-methyl-6-trifluoromethylpyrimidin-4-yloxy) propionic acid (1.0 g) dissolved in tetrahydrofuran (30 ml), at room temperature, and the mixture was stirred for 30 min. Subsequently, 2-amino-2,3,3-trimethylbutyronitrile (0.5 g) was added to the mixture, and the reaction mixture was stirred for 10 hours at room temperature. After completion of the reaction, water was added to the resulting mixture and the organic layer was extracted with ethyl acetate, and subsequently dried over anhydrous magnesium sulfate. The ethyl acetate was removed under reduced pressure. The residue was purified by column chromatography on silica gel to give 0.3 g of the A-configurational diastereomer having a melting point of 1 33° C. to 1 34° C. and 0.2 g of the B-configurational diastereomer having a melting point of 137° C. to 139° C.

PREPARATION EXAMPLE 5

Synthesis of 2-(5-chloro-6-isopropylpyrimidin-4-ylthio)-N-(1-cyano-1,2-dimethylpropyl)propionamide (Compound No. B-17)

60% Sodium hydride (0.1 g) was washed with hexane and then suspended in dimethylformamide (20 ml). 5-Chloro-6-isopropyl-4-mercaptopyrimidine (0.2 g) was added to the suspension in a dropwise manner, and subsequently the mixture was stirred for an hour at room temperature. Subsequently, N-(1-cyano-1,2-dimethylpropyl)-2-bromopropionamide (0.3 g) was added thereto in a dropwise manner, and the reaction mixture was stirred for 3 hours at room temperature. After completion of the reaction, water was added to the reaction liquid. The organic layer was extracted with ethyl acetate and was then dried over anhydrous magnesium sulfate. The ethyl acetate was removed under reduced pressure. The residue was purified by column chromatography on silica gel to give 0.3 g of the desired product having a melting point of 73° C. to 75° C.

PREPARATION EXAMPLE 6

Synthesis of 2-(2-alkylthio-6-trifluloromethylpyrimidin-4-yloxy)-N-(1-cyano-1,2-dimethylpropyl)propionamide (Compound No. A-25 1)

N-(1-cyano-1,2-dimethylpropyl)-2-hydroxypropionamide (1.0 g) was dissolved in tetrahydrofuran (30 ml). 60% Sodium hydride (0.2 g) was added to the solution, and subsequently the mixture was stirred for 30 minutes at room temperature. Subsequently, 2-alkylthio-4-chloro-6-trifluoromethylpyrimidine (0.7 g) was added to the mixture, and then the reaction mixture was stirred for 6 hours at room temperature. After completion of the reaction, water was added to the reaction liquid. Subsequently, the organic layer was extracted with ethyl acetate and was then dried over anhydrous magnesium sulfate. The ethyl acetate was removed under reduced pressure. The residue was purified by column chromatography on silica gel to give 1.1 g of the desired product having a melting point of 96° C. to 98° C.

PREPARATION EXAMPLE 7

Synthesis of 2-(5-chloro-2-methyl-6-trifluoromethylpyrimidin-4-yloxy)-N-(1-isopropyl-1-methyl-2-oxopropyl)propionamide (Compound No. A-334)

1-Ethyl-3-(3-dimethylaminnopropyl)carbodiimide hydrochloride (0.7 g) was added to a solution containing 2-(5-chloro-2-methyl-6-trifluoromethylpyrimidin-4-yloxy) propionic acid (0.9 g) dissolved in dichloromethane (20 ml), at room temperature, and the mixture was stirred for 10 min. Subsequently, 3-amino-3,4-dimethyl-2-pentanone (0.4 g) was added to the mixture, and the reaction mixture was stirred for 3 hours at room temperature. After completion of the reaction, water was added to the resulting mixture and the dichloromethane layer was washed with water, and subsequently dried over anhydrous magnesium sulfate. The dichloromethane was removed under reduced pressure. The residue was purified by column chromatography on silica gel to give 0.8 g of the desired product having a melting point of 124° C. to 126° C.

The agricultural or horticultural fungicides according to the present invention include pyrimidinyloxyalkanamide derivatives represented by Formula (I) as active ingredients. In the case where the compounds according to the present invention are employed as agricultural or horticultural fungicides, the compounds acting as the active ingredients can be formulated appropriately, depending on the purpose. The active ingredient is usually diluted in an inert liquid or a solid carrier, and a surfactant and the like are added thereto, if necessary. The mixture is then formulated in a known manner into, for example, a fine powder, a wettable powder, an emulsifiable concentrate, granules, or the like.

As the suitable carriers employed in the formulation, there can be mentioned solid carriers such as talc, bentonite, clay, kaolin, diatomaceous earth, white carbon, vermiculite, slaked lime, siliceous sand, ammonium sulfate, urea, or the like; and liquid carriers such as isopropyl alcohol, xylene, cyclohexanone, methylnaphthalene, and the like. As the surfactants and dispersants, there can be mentioned, for example, dinaphthylmethane disulfonate, alcohol sulfates, alkyl aryl sulfonates, lignin sulfonates, polyoxyetliylene glycol ethers, polyoxyethylene alkyl aryl ethers, polyoxycthylene sorbitan monoalkylates, and the like. As auxiliary agents, there can be mentioned carboxymethyl cellulose, and the like. The formulated agricultural or horticultural fungicide according to the present invention can be spread in an appropriately diluted concentration or can be applied directly.

The agricultural or horticultural fungicides according to the present invention can be employed for spraying stem and leaf portions, application to soil, and submerged application. The proportion of the active ingredient is selected as needed. When formulated into a fine powder or granules, 0.1% by weight to 20% by weight of the active ingredient are preferred. For an emulsifiable concentrate or wettable powder, 5% by weight to 80% by weight of the active ingredient are preferred.

The rate of application of the agricultural or horticultural fungicide according to the present invention may vary depending on the kind of the compound, the kind of the pest or disease to be controlled, the nature of occurrence of the pest or disease, the degree of damage, environmental conditions, the form of preparation to be used, and the like. When the agricultural or horticultural fungicides of the present invention are applied directly in the form of fine powder or granules, it is recommended that the rate of application of the active ingredient be suitably chosen within the range of 0.1 g to 5 kg per 10 ares, and preferably, in the range of 1 g to 1 kg per 10 ares. In addition, when the fungicides of the present invention are in the form of a liquid such as an emulsifiable concentrate or a wettable powder, it is recommended that the ratio for application of the active ingredient be suitably chosen within the range of 0.1 ppm to 10,000 ppm, and preferably within the range of 1 ppm to 3,000 ppm.

The agricultural or horticultural fungicide of the present invention can control plant diseases caused by the pathogenic fungi in the Oomrycetes, Ascomycetes, Deuteromiycetes, and Basidiomycetes in the formulation mentioned above. In the following, examples of the fungi will be listed, but are not limited thereto: Pseudoperonospora such as downy mildew fungi (*Pseudoperonospora cubensis*), Sphaerotheca such as powdery mildew fungi (*Sphaerotheca fuliginea*), Venturia such as apple scab fungi (*Venturia inaequalis*), Pyricularia such as rice blast fungi (*Pyricularia oryzace*), Gibberella such as "Bakanae" disease fungi (*Gibberella fujikturoi*), Botrytis such as gray mold fungi (*Botrytis cinerea*), Alteriiaria such as chinese mustard sooty spot fungi (*Alternaria brassicicola*), Rhizoctotnia such as rice sheath blight fungi (*Rhizoctonia solani*), and Pucciniia such as rust fungi (*Puccinia recondita*).

In addition, the compound according to the present invention may be employed alone or in combination with other fungicides, insecticides, herbicides, plant growth modifiers, fertilizers or the like. Next, the representative formulations are illustrated with reference to the following Formulation Examples, wherein all "%" represent "percent by weight".

Formulation Example 1

Fine Powder

2% of Compound No. A-1, 5% of diatomaceous earth, and 93% of clay were uniformly mixed and ground into a fine powder.

Formulation Example 2

Wettable Powder

50% of Compound No. A-7, 45% of diatomaceous earth, 2% of sodium dinaphthylmethane disulfonate, and 3% of sodium ligninsulfonate were uniformly mixed and ground into a wettable powder.

Formulation Example 3

Emulsifiable Concentrate

30% of Compound No. A-12, 20% of cyclohexanone, 11% of polyoxyethylene alkyl aryl ether, 4% of calcium alkylbenzenesulfonate, and 35% of methylnaphthalene were uniformly emulsified, thus yielding an emulsifiable concentrate.

Formulation Example 4

Granules

5% of Compound No. B-5, 2% of sodium salt of lauryl alcohol sulfate, 5% of sodium ligninsulfonate, 2% of carboxymethyl cellulose, and 86% of clay were mixed and ground. Water was added to the ground mixture, in an amount of 20% based on the total weight of the ground mixture. The resulting mixture was kneaded and formed into granules of 14 mesh to 32 mesh by means of an extrusion granulator, and then dried into the desired granules.

In the following, the effects exhibited by the agricultural or horticultural fungicides according to the present invention will be explained by reference to Test Examples. In Test Examples, N-(1-cyano-1,2-dimethylpropyl)-2-(pyrimidin-2-yloxy)propionamide disclosed in Japanese Patent Application, First Publication, No. Sho 63-132867, was employed as a comparative compound.

Test Example 1

Test on the Preventive Effects for Rice Blast (*Pyricularia oryzae*)

Paddy rice seeds (variety: Aichi Asahi) were sown at a rate of approximately 15 grains each in porcelain pots having a diameter of 7 cm. The seeds were allowed to germinate and grow for 2 to 3 weeks in a greenhouse. A wettable powder prepared according to Formulation Example 2 was diluted with water to a concentration of 500 ppm of the active ingredient, and subsequently the obtained aqueous preparation was sprayed at a rate of 10 ml per pot on the rice seedlings at their 4-leaf stage. After being dried in the air, the seedlings were inoculated by spraying a conidiospore suspension of rice blast fungi (*Pyricularia oryzae*) and immediately placed in a moist chamber at 25° C. for 24 hours and subsequently in a greenhouse. On the fifth day after the inoculation, the number of lesions on the fourth leaf was counted. The controlling activity was calculated according to Equation 1. The evaluation results obtained according to the Evaluation Standard shown in Table 17 are shown in Tables 18 to 21.

$$\text{Controlling Activity (\%)} = \left(1 - \frac{\text{the Number of Lesions in Treated Plot}}{\text{the number of Lesions in Untreated Plot}}\right) \times 100 \quad \text{Equation 1}$$

TABLE 17

| Evaluation | Controlling Activity |
|---|---|
| A | 100% |
| B | 80.0% or more and less than 100% |
| C | 50.0% or more and less than 80.0% |
| D | less than 50.0% |

TABLE 18

| Compound No. | Evaluation | Compound No. | Evaluation |
|---|---|---|---|
| A-1 | A | A-66 | A |
| A-5 | A | A-68 | B |
| A-6 | A | A-69 | B |
| A-7 | A | A-70 | B |
| A-12 | B | A-71 | B |
| A-13 | B | A-72 | B |
| A-15 | B | A-73 | B |
| A-16 | B | A-74 | B |
| A-18 | B | A-75 | A |
| A-21 | B | A-76 | B |
| A-22 | B | A-77 | B |
| A-25 | A | A-78 | A |
| A-26 | A | A-79 | B |
| A-27 | A | A-80 | B |
| A-28 | B | A-81 | B |
| A-31 | B | A-82 | B |
| A-32 | B | A-83 | B |
| A-36 | A | A-88 | B |
| A-38 | A | A-89 | B |
| A-39 | B | A-90 | B |
| A-40 | B | A-91 | B |
| A-41 | B | A-93 | A |
| A-42 | B | A-94 | B |
| A-43 | B | A-95 | A |
| A-44 | A | A-96 | A |
| A-49 | A | A-98 | A |
| A-54 | A | A-99 | A |
| A-55 | B | A-100 | B |
| A-58 | B | A-101 | A |
| A-59 | B | A-109 | B |
| A-61 | B | A-110 | B |
| A-62 | B | A-111 | B |
| A-63 | B | A-112 | B |
| A-64 | A | A-113 | B |
| A-65 | A | A-114 | B |

TABLE 19

| Compound No. | Evaluation | Compound No. | Evaluation |
|---|---|---|---|
| A-116 | B | A-199 | B |
| A-125 | B | A-200 | B |
| A-128 | A | A-201 | B |
| A-129 | A | A-202 | B |
| A-132 | B | A-203 | B |
| A-136 | B | A-204 | B |
| A-137 | B | A-205 | B |
| A-141 | A | A-208 | B |
| A-142 | A | A-210 | B |
| A-143 | A | A-214 | B |
| A-144 | B | A-215 | B |
| A-145 | B | A-216 | B |
| A-149 | A | A-219 | A |
| A-150 | A | A-220 | B |
| A-151 | A | A-223 | B |
| A-152 | A | A-224 | A |
| A-153 | A | A-225 | A |
| A-156 | A | A-227 | A |
| A-157 | A | A-228 | A |
| A-158 | B | A-229 | A |
| A-159 | B | A-236 | B |
| A-166 | A | A-237 | B |
| A-167 | A | A-238 | B |
| A-168 | B | A-239 | B |
| A-169 | B | A-240 | B |
| A-172 | B | A-241 | A |
| A-176 | B | A-242 | A |
| A-177 | A | A-246 | B |
| A-183 | B | A-247 | B |
| A-184 | B | A-248 | B |
| A-192 | B | A-249 | B |
| A-193 | B | A-250 | B |

TABLE 19-continued

| Compound No. | Evaluation | Compound No. | Evaluation |
|---|---|---|---|
| A-194 | B | A-251 | A |
| A-195 | B | A-252 | B |
| A-196 | B | A-253 | A |

TABLE 20

| Compound No. | Evaluation | Compound No. | Evaluation |
|---|---|---|---|
| A-254 | B | A-294 | A |
| A-255 | A | A-295 | A |
| A-256 | A | A-296 | A |
| A-257 | B | A-297 | A |
| A-258 | A | A-298 | A |
| A-259 | A | A-299 | A |
| A-260 | A | A-300 | A |
| A-261 | A | A-301 | A |
| A-262 | A | A-302 | B |
| A-263 | A | A-303 | B |
| A-264 | B | A-304 | B |
| A-265 | A | A-305 | A |
| A-266 | A | A-306 | B |
| A-267 | B | A-307 | B |
| A-268 | A | A-308 | A |
| A-269 | A | A-309 | A |
| A-270 | A | A-310 | B |
| A-274 | B | A-311 | A |
| A-275 | B | A-312 | B |
| A-276 | A | A-313 | B |
| A-277 | A | A-314 | B |
| A-278 | A | A-315 | B |
| A-279 | A | A-316 | B |
| A-280 | A | A-317 | B |
| A-281 | A | A-318 | A |
| A-282 | A | A-319 | B |
| A-283 | A | A-320 | B |
| A-284 | A | A-321 | A |
| A-285 | A | A-322 | B |
| A-286 | B | A-323 | A |
| A-287 | A | A-324 | A |
| A-288 | A | A-325 | A |
| A-291 | A | A-326 | A |
| A-292 | A | A-327 | A |
| A-293 | B | A-328 | A |

TABLE 21

| Compound No. | Evaluation | Compound No. | Evaluation |
|---|---|---|---|
| A-330 | A | B-1 | B |
| A-333 | A | B-2 | B |
| A-334 | A | B-3 | B |
| A-335 | A | B-5 | A |
| A-336 | A | B-6 | B |
| A-337 | A | B-7 | A |
| A-338 | B | B-10 | A |
| A-339 | B | B-11 | A |
| A-340 | B | B-14 | A |
| A-341 | B | B-15 | B |
| A-342 | A | B-17 | B |
| A-343 | B | B-18 | B |
| A-344 | B | B-21 | B |
| A-345 | A | B-22 | B |
| A-346 | B | B-25 | A |
| A-347 | B | B-26 | B |
| A-348 | B | B-28 | B |
| A-349 | B | B-29 | B |
| A-350 | B | Comparative compound | D |
| A-354 | B | | |
| A-355 | B | | |
| A-356 | B | | |
| A-360 | A | | |
| A-361 | B | | |
| A-362 | B | | |

Test Example 2

Test on the Submerged Application Effects on Rice Blast (*Pyricularia oryzae*)

Paddy rice seedlings (variety: Aichi Asahi) at their 1.5-leaf stage were transplanted at 4 locations at a rate of 3 seedlings per location each in white porcelain pots having a diameter of 9 cm. The seedlings were allowed to germinate and grow in a greenhouse. When the seedlings grew to the 2.5-leaf stage, wettable powders prepared according to Formulation Example 2 were applied into the irrigation water in the pot so that the concentration of the active ingredient was at 300 g per 10 ares. After 10 days from the treatment, the seedlings were inoculated by spraying a conidospore suspension of rice blast fungi (*Pyricularia oryzae*) and immediately placed in a moist chamber at 25° C. for 24 hours and subsequently in a greenhouse so as to induce an attack of the disease. On the fifth day after the inoculation, the number of lesions on the leaf which was in the most advanced stage of development at the time of the inoculation was counted. The controlling activity was calculated according to Equation 1. The evaluation results obtained according to the Evaluation Standard shown in Table 17 are shown in Tables 22 and 23.

TABLE 22

| Compound No. | Evaluation | Compound No. | Evaluation |
|---|---|---|---|
| A-6 | A | A-129 | B |
| A-7 | B | A-141 | B |
| A-18 | A | A-144 | B |
| A-21 | A | A-149 | B |
| A-25 | B | A-150 | B |
| A-31 | A | A-151 | B |
| A-39 | B | A-158 | A |
| A-41 | A | A-166 | B |
| A-42 | B | A-196 | B |
| A-43 | B | A-199 | B |
| A-49 | B | A-219 | B |
| A-64 | A | A-220 | B |
| A-65 | B | A-223 | B |
| A-66 | B | A-227 | B |
| A-68 | B | A-241 | B |
| A-69 | B | A-251 | A |
| A-70 | B | A-254 | B |
| A-74 | B | A-255 | B |
| A-75 | B | A-258 | B |
| A-76 | B | A-259 | A |
| A-77 | B | A-260 | A |
| A-78 | B | A-261 | A |
| A-81 | B | A-263 | A |
| A-82 | B | A-264 | B |
| A-91 | A | A-266 | B |
| A-93 | A | A-267 | A |
| A-95 | B | A-268 | B |
| A-109 | A | A-269 | A |
| A-110 | B | A-270 | A |
| A-111 | A | A-275 | B |
| A-112 | A | A-276 | A |
| A-113 | A | A-277 | B |
| A-114 | A | A-278 | B |
| A-116 | A | A-282 | A |
| A-128 | A | A-283 | B |

TABLE 23

| Compound No. | Evaluation |
| --- | --- |
| A-284 | B |
| A-288 | A |
| A-291 | A |
| A-292 | A |
| A-294 | A |
| A-295 | B |
| A-296 | A |
| A-297 | A |
| A-298 | A |
| A-299 | A |
| A-300 | A |
| A-301 | A |
| A-318 | A |
| A-323 | A |
| A-325 | B |
| A-330 | A |
| A-333 | A |
| A-334 | A |
| A-335 | A |
| A-342 | B |
| A-360 | B |
| B-5 | B |
| B-10 | B |
| Comparative compound | D |

What is claimed is:

1. A pyrimidinyloxyalkanamide compound represented by Formula (1):

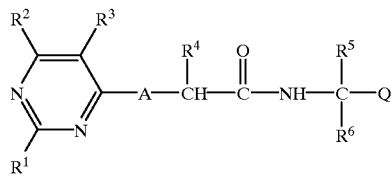

(I)

wherein $R^1$ represents a hydrogen atom, a $C_1$–$C_6$ alkyl group, a $C_3$–$C_6$ cycloalkyl group, a $C_1$–$C_4$ haloalkyl group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a $C_1$–$C_6$ alkylthio group, a $C_1$–$C_6$ alkylsulfinyl group, a $C_1$–$C_6$ alkylsulfonyl group, a $C_2$–$C_6$ alkenylthio croup, a $C_2$–$C_6$ alkynylthio group, a $C_3$–$C_6$ cycloalkylthio group, a $C_1$–$C_6$ alkylamino group, a di($C_1$–$C_6$)alkylamino group, a halogen atom, a phenyl group which may be substituted by a $C_1$–$C_6$ alkyl group, a $C_1$–$C_4$ haloalkyl group, a $C_1$–$C_6$ alkoxy group, a cyano group, a nitro group, or a halogen atom, or a phenoxy group which may be substituted by a $C_1$–$C_6$ alkyl group, a $C_1$–$C_4$ haloalkyl group, a $C_1$–$C_6$ alkoxy group, a cyano group, a nitro group, or a halogen atom, $R^2$ represents a hydrogen atom, a $C_1$–$C_6$ alkyl group, a $C_2$–$C_6$ alkenyl group, a $C_2$–$C_6$ alkynyl group, a $C_3$–$C_6$ cycloalkyl group, a $C_1$–$C_4$ haloalkyl group, a $C_2$–$C_6$ haloalkenyl group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a $C_1$–$C_4$ haloalkoxy group, a $C_1$–$C_6$ alkylthio group, a $C_2$–$C_6$ alkenylthio group, a $C_2$–$C_6$ alkynylthio group, a $C_1$–$C_6$ alkylamino group, a di$C_1$–$C_6$ alkylamino group, a halogen atom, or a phenyl group which may be substituted by a $C_1$–$C_6$ alkyl group, a $C_1$–$C_4$ haloalkyl group, a $C_1$–$C_6$ alkoxy group, a cyano group, a nitro group, or a halogen atom, $R^3$ represents a hydrogen atom, a $C_1$–$C_6$ alkyl group, a $C_3$–$C_6$ cycloalkyl group, a $C_1$–$C_4$ haloalkyl group, a $C_1$–$C_6$ alkoxy group, a $C_1$–$C_6$ alkylcarbonyl group, a $C_1$–$C_6$ alkoxy carbonyl group, a halogen atom, a nitro group, or a cyano group, or $R^2$ and $R^3$, together with the carbon atom to which they are bonded, form a saturated 6-membered ring, or an unsaturated 5-membered or 6-membered ring, $R^4$ represents a hydrogen atom, a $C_1$–$C_6$ alkyl group, a $C_3$–$C_6$ cycloalkyl group, or a $C_1$–$C_4$ haloalkyl group, $R^5$ and $R^6$ represents independently a hydrogen atom, a $C_1$–$C_6$ alkyl group, a $C_2$–$C_6$ alkenyl group, a $C_3$–$C_6$ cycloalkyl group which may be substituted by a halogen atom or a $C_1$–$C_6$ alkyl group, a $C_3$–$C_6$ cycloalkyl $C_1$–$C_6$ alkyl group, a $C_1$–$C_6$ alkoxy $C_1$–$C_6$ alkyl group, or a $C_1$–$C_4$ haloalkyl group, $R^5$ and $R^6$, together with the carbon atom to which they are bonded, form a 5 to 7 membered cycloalkyl group which may be substituted by a $C_1$–$C_6$ alkyl group, or a hetrocyclyl group which may be substituted by a $C_1$–$C_6$ alkyl group, Q represents a cyano group or a group of a formula: —$COR^7$ wherein $R^7$ represents a $C_1$–$C_6$ alkyl group, a $C_3$–$C_6$ cycloalkyl group which may be substituted by a halogen atom or a $C_1$–$C_6$ alkyl group, a $C_1$–$C_4$ haloalkyl group, a $C_1$–$C_6$ alkoxy group, a $C_2$–$C_6$ alkenyloxy group, a $C_2$–$C_6$ alkynyloxy group, or a $C_3$–$C_6$ cycloalkyloxy group, and A represents an oxygen atom or a sulfur atom.

2. A pyrimidinyloxyalkanamide compound represented by Formula (1):

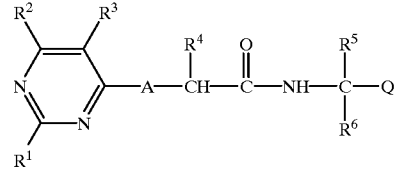

(I)

wherein $R^1$ represents a hydrogen atom, a $C_1$–$C_6$ alkyl group, a $C_3$–$C_6$ cycloalkyl group, a $C_1$–$C_4$ haloalkyl group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a $C_1$–$C_6$ alkylthio group, a $C_1$–$C_6$ alkylsulfinyl group, a $C_1$–$C_6$ alkylsulfonyl group, a $C_2$–$C_6$ alkenylthio croup, a $C_2$–$C_6$ alkynylthio group, a $C_3$–$C_6$ cycloalkylthio group, a halogen atom, a phenyl group which may be substituted by a $C_1$–$C_6$ alkyl group, a $C_1$–$C_4$ haloalkyl group, a $C_1$–$C_6$ alkoxy group, a cyano group, a nitro group, or a halogen atom, or a phenoxy group which may be substituted by a $C_1$–$C_6$ alkyl group, a $C_1$–$C_4$ haloalkyl group, a $C_1$–$C_6$ alkoxy group, a cyano group, a nitro group, or a halogen atom, $R^2$ represents a $C_1$–$C_6$ alkyl group, a $C_2$–$C_6$ alkenyl group, a $C_2$–$C_6$ alkynyl group, a $C_3$–$C_6$ cycloalkyl group, a $C_1$–$C_4$ haloalkyl group, a $C_2$–$C_6$ haloalkenyl group, a $C_1$–$C_6$ alkoxy group, a $C_2$–$C_6$ alkenyloxy group, a $C_2$–$C_6$ alkynyloxy group, a $C_3$–$C_6$ cycloalkyloxy group, a $C_1$–$C_4$ haloalkoxy group, a $C_1$–$C_6$ alkylthio group, a $C_2$–$C_6$ alkenylthio group, a $C_2$–$C_6$ alkynylthio group, or a halogen atom, $R^3$ represents a hydrogen atom, a $C_1$–$C_6$ alkyl group, a $C_3$–$C_6$ cycloalkyl group, a $C_1$–$C_4$ haloalkyl group, a $C_1$–$C_6$ alkoxy group, a halogen atom, or a cyano group, or R² and R³, together with the carbon atom to which they are bonded, form a saturated 6-membered ring or an unsaturated 5-membered or 6-membered ring, R⁴ represents a hydrogen atom, a $C_1$–$C_6$ alkyl group, or a $C_3$–$C_6$ cycloalkyl group, R⁵ and R⁶ represents independently a hydrogen atom, a $C_1$–$C_6$ alkyl group, a $C_2$–$C_6$ alkenyl group, a $C_3$–$C_6$ cycloalkyl group which may be substituted by a halogen atom or a $C_1$–$C_6$ alkyl group, a $C_1$–$C_6$ alkoxy $C_1$–$C_6$ alkyl group, or a $C_1$–$C_4$ haloalkyl group, R⁵ and R⁶, together with the carbon atom to which they are bonded, form a 5 to 7 membered cycloalkyl group which may be substituted by a $C_1$–$C_6$ alkyl group, or a hetrocyclyl group which may be substituted by a $C_1$–$C_6$ alkyl group, Q represents a cyano group or a group of a formula: —COR⁷ wherein R⁷ represents a $C_1$–$C_6$ alkyl group, a $C_3$–$C_6$ cycloalkyl group which may be substituted by a halogen atom or a $C_1$–$C_6$ alkyl group, a $C_1$–$C_4$ haloalkyl group, a $C_1$–$C_6$ alkoxy group, a $C_2$–$C_6$ alkenyloxy group, a $C_2$–$C_6$ alkynyloxy group, or a $C_3$–$C_6$ cycloalkyloxy group, and A represents an oxygen atom or a sulfur atom.

3. A pyrimidinyloxyalkanamide compound represented by Formula (1):

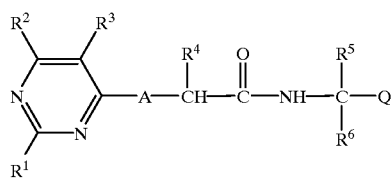

(I)

wherein R¹ represents a hydrogen atom, a $C_1$–$C_6$ alkyl group, a $C_3$–$C_6$ cycloalkyl group, a $C_1$–$C_4$ haloalkyl group, a $C_1$–$C_6$ alkoxy group, a $C_{C6}$ alkylthio group, a $C_2$–$C_6$ alkenylthio group, a $C_2$–$C_6$ alkynylthio group, a halogen atom, a phenyl group, or a phenoxy group, R² represents a $C_1$–$C_6$ alkyl group, a $C_1$–$C_4$ haloalkyl group, a $C_1$–$C_6$ alkoxy group, a $C_1$–$C_6$ alkylthio group, or a halogen atom, R³ represents a hydrogen atom, a $C_1$–$C_6$ alkyl group, or a halogen atom, R⁴ represents a hydrogen atom or a $C_1$–$C_6$ alkyl group, R⁵ and R⁶ represents independently a hydrogen atom, a $C_1$–$C_6$ alkyl group, a $C_3$–$C_6$ cycloalkyl group, or a $C_1$–$C_4$ haloalkyl group, R⁵ and R⁶, together with the carbon atom to which they are bonded, folm a 5 to 7 membered cycloalkyl group which may be substituted by a $C_1$–$C_6$ alkyl group, Q represents a cyano group or a group of a formula: —COR⁷ wherein R⁷ represents a $C_1$–$C_6$ alkyl group, a $C_3$–$C_6$ cycloalkyl group, or a $C_1$–$C_6$ alkoxy group, and A represents an oxygen atom or a sulfur atom.

4. A fungicidal composition, comprising a fungicidally effective amount of the pyrimidinyloxyalkanamide compound as recited in claim 1 and a carrier.

5. A fungicidal composition, comprising a fungicidally effective amount of the pyrimidinyloxyalkanamide compound as recited in claim 2 and a carrier.

6. A method of treating plants, comprising applying the a fungicidally effective amount of pyrimidinyloxyalkanamide compound as recited in claim 1 to plants.

7. A method of treating plants, comprising applying the pyrimidinyloxyalkanamide compound as recited in claim 2 to plants.

8. The fungicidal composition of claim 4, wherein the effective amount of the pyrimidinyloxyalkanamide is 5% to 80% by weight.

9. The fungicidal composition of claim 4, wherein the effective amount of the pyrimidinyloxyalkanamide is 0.1% to 20% by weight.

10. The fungicidal composition of claim 5, wherein the effective amount of the pyrimidinyloxyalkanamide is 5% to 80% by weight.

11. The fungicidal composition of claim 5, wherein the effective amount of the pyrimidinyloxyalkanamide is 0.1% to 20% by weight.

12. The method of claim 6, wherein the rate if applying the fungicidal composition is 0.1 g to 5 kg per acre of plants.

13. The method of claim 12, wherein the rate of applying the fungicidal composition is 1 g to 1 kg per acre of plants.

14. The method of claim 7, wherein the rate if applying the fungicidal composition is 0.1 g to 5 kg per acre of plants.

15. The method of claim 14, wherein the rate of applying the fungicidal composition is 1 g to 1 kg per acre of plants.

16. A compound selected from:
2-5-chloro-6-ethylpyrimidin-4-yoloxy)-N-(1-cyano-1,2-dimethylpropyl)acetamide;
ethyl 2-(5-chloro-6-ethylpyrimidin-4-yoxy)acetate;
2-(5-chloro-6-ethylpyrimidin-4-yloxy)acetic acid);
2-(1-(5-chloro-6-trifluoromethylpyrimidin-4-yloxy)-thylcarbonylamino)-2,3-dimethylbutyrate;
ethyl 2-(5-chloro-6-trifluoromethylpyrimidin-4-yloxy) propionate;
2-(5-chloro-6-trifluoromethylpyrimidin-4-yloxy)propionic acid;
2-(5-chloro-6-trifluoromethylpyrimidin-4-yloxy)-N-(1-cyanocyclopentyl)propionamide;
2-(5-chloro-2-methyl-6-trifluoromethylpyrimidin-4-yloxy)-N-(1-cyano-1,2,2-trimethylpropyl)propionamide;
2-(5-chloro-6-isopropylpyrimidin-4-ylthio)-N-(1-cyano-1,2-dimethylpropyl)propionamide;
2-(2-alkylthio-6-trifluoromethylpyrimidin-4-yloxy)-N-(1-cyano-1,2-dimethylpropyl)propionamide;
2-(5-chloro-2-methyl-6-trifluoromethylpyrimidin-4-yloxy)-N-(1-isopropyl-1-methyl-2-oxopropyl)propionamide, or mixture thereof.

17. A fungicidal composition, comprising a fungicidally effective amount of the compound as recited in claim 16 and a carrier.

18. A method of treating plants, comprising applying the a fungicidally effective amount of compound as recited in claim 16 to plants.

19. The fungicidal composition of claim 17, wherein the effective amount of the pyrimidinyloxyalkanamide is 5% to 80% by weight.

20. The fungicidal composition of claim 17, wherein the effective amount of the pyrimidinyloxyalkanamide is 0.1% to 20 % by weight.

21. The method of claim 18, wherein the rate if applying the fungicidal composition is 0.1 g to 5 kg per acre of plants.

22. The method of claim 13, wherein the rate of applying the fungicidal composition is 1 g to 1 kg per acre of plants.

* * * * *